United States Patent
Iwane

(10) Patent No.: US 12,004,723 B2
(45) Date of Patent: Jun. 11, 2024

(54) ENDOSCOPE SYSTEM FOR CONTROLLING AN AMOUNT OF ILLUMINATION LIGHT

(71) Applicant: FUJIFILM Corporation, Tokyo (JP)

(72) Inventor: Kosuke Iwane, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 461 days.

(21) Appl. No.: 17/400,877

(22) Filed: Aug. 12, 2021

(65) Prior Publication Data
US 2021/0369096 A1  Dec. 2, 2021

Related U.S. Application Data

(63) Continuation of application No. PCT/JP2020/006020, filed on Feb. 17, 2020.

(30) Foreign Application Priority Data

Feb. 19, 2019  (JP) ................................. 2019-027187

(51) Int. Cl.
*A61B 1/06* (2006.01)
*A61B 1/00* (2006.01)
*A61B 1/04* (2006.01)

(52) U.S. Cl.
CPC ...... *A61B 1/0638* (2013.01); *A61B 1/000094* (2022.02); *A61B 1/0655* (2022.02); *A61B 1/00006* (2013.01); *A61B 1/043* (2013.01)

(58) Field of Classification Search
None
See application file for complete search history.

(56) References Cited

U.S. PATENT DOCUMENTS

2004/0162492 A1* 8/2004 Kobayashi ............. A61B 1/043
                                                          382/128
2007/0010713 A1   1/2007 Negishi
(Continued)

FOREIGN PATENT DOCUMENTS

CN       1572229 A    2/2005
CN     101288581 A   10/2008
(Continued)

OTHER PUBLICATIONS

An Office Action mailed by China National Intellectual Property Administration on Dec. 2, 2022, which corresponds to Chinese Patent Application No. 202080015266.7 and is related to U.S. Appl. No. 17/400,877; with English language translation.
(Continued)

*Primary Examiner* — John P Leubecker
(74) *Attorney, Agent, or Firm* — Studebaker & Brackett PC

(57) ABSTRACT

An endoscope system that controls an amount of illumination light according to a change of a subject where the subject is illuminated with a plurality of pieces of light while the plurality of pieces of light are switched. The system includes a light source unit that emits first illumination light and second illumination light having an emission spectrum different from an emission spectrum of the first illumination light, a first processor, and a second processor. A set light amount-adjustment unit performs at least one of adjustment of the amount of second illumination light that is set at a first switching timing at which illumination light is switched to the second illumination light from first illumination light or adjustment of the amount of first illumination light that is set at a second switching timing at which illumination light is switched to the first illumination light from second illumination light.

11 Claims, 12 Drawing Sheets

(56) References Cited

U.S. PATENT DOCUMENTS

| | | | |
|---|---|---|---|
| 2007/0010714 A1 | 1/2007 | Negishi | |
| 2007/0213593 A1* | 9/2007 | Nakaoka | A61B 1/00186 600/181 |
| 2008/0262299 A1 | 10/2008 | Niida et al. | |
| 2009/0147078 A1 | 6/2009 | Tani et al. | |
| 2012/0016200 A1 | 1/2012 | Seto et al. | |
| 2015/0065802 A1 | 3/2015 | Ozawa et al. | |
| 2017/0231502 A1* | 8/2017 | Nagaoka | A61B 1/0684 600/476 |

FOREIGN PATENT DOCUMENTS

| | | | |
|---|---|---|---|
| CN | 101943796 A | 1/2011 | |
| CN | 102334972 A | 2/2012 | |
| EP | 1488731 A1 | 12/2004 | |
| JP | 2011-250926 A | 12/2011 | |
| JP | 2012-000160 A | 1/2012 | |
| JP | 2015-062656 A | 4/2015 | |
| JP | 2015-173737 A | 10/2015 | |
| JP | 2016-152920 A | 8/2016 | |
| JP | 2017-012637 A | 1/2017 | |
| JP | 2017-185258 A | 10/2017 | |
| JP | 2017-202241 A | 11/2017 | |
| WO | 2016/080130 A1 | 5/2016 | |

OTHER PUBLICATIONS

International Search Report issued in PCT/JP2020/006020; mailed Apr. 21, 2020.

Written Opinion issued in PCT/JP2020/006020; mailed Apr. 21, 2020.

An Office Action mailed by China National Intellectual Property Administration on Apr. 27, 2023, which corresponds to Chinese Patent Application No. 202080015266.7 and is related to U.S. Appl. No. 17/400,877; with English language translation.

An Office Action; "Notice of Reasons for Refusal", mailed by the Japanese Patent Office on Jul. 5, 2022, which corresponds to Japanese Patent Application No. 2021-501977 and is related to U.S. Appl. No. 17/400,877; with English language translation.

* cited by examiner

FIRST ILLUMINATION LIGHT

SECOND ILLUMINATION LIGHT

FIG. 9
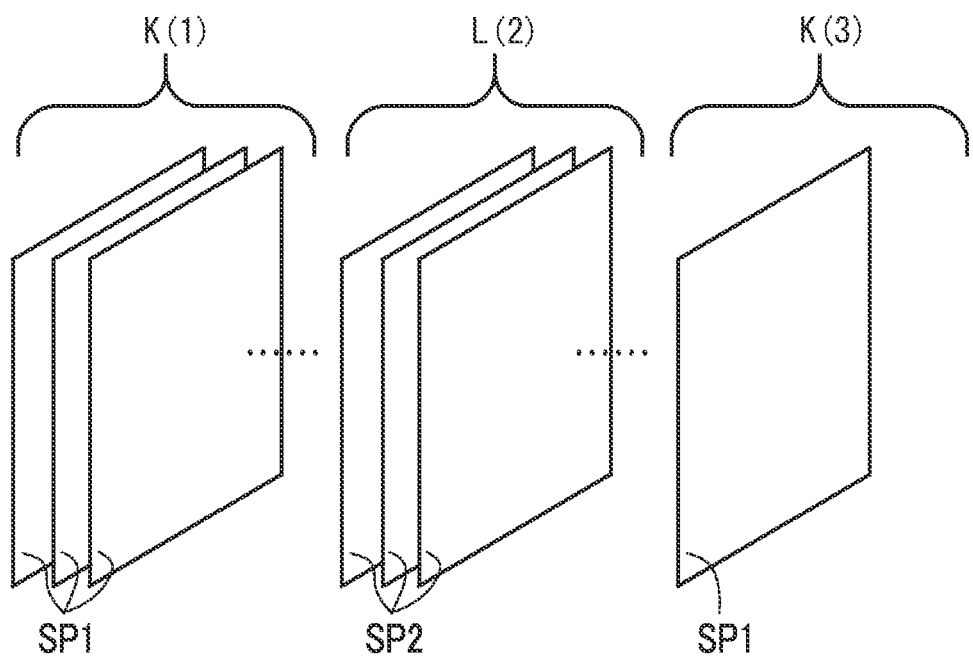
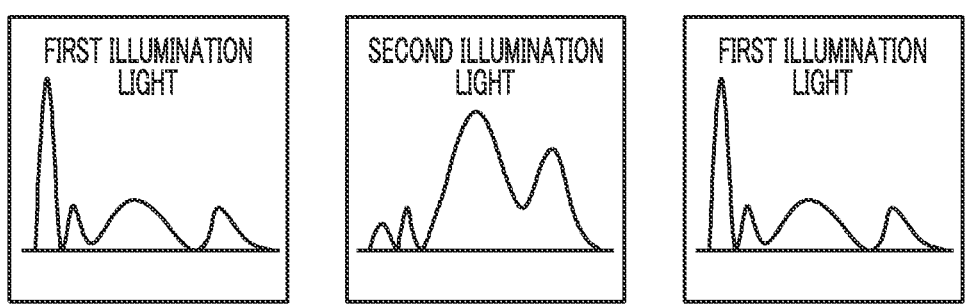
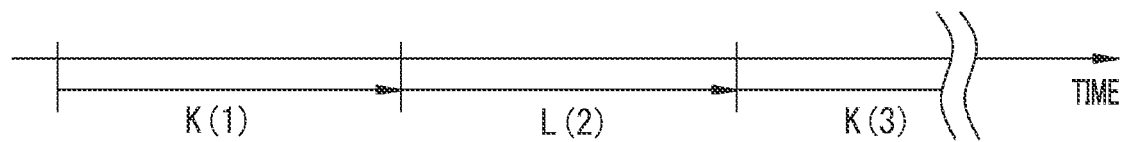

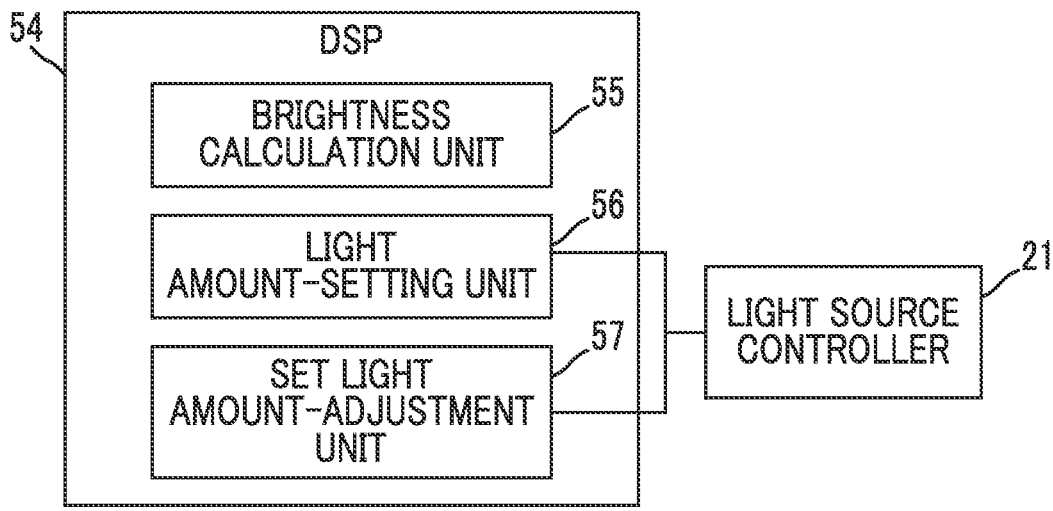
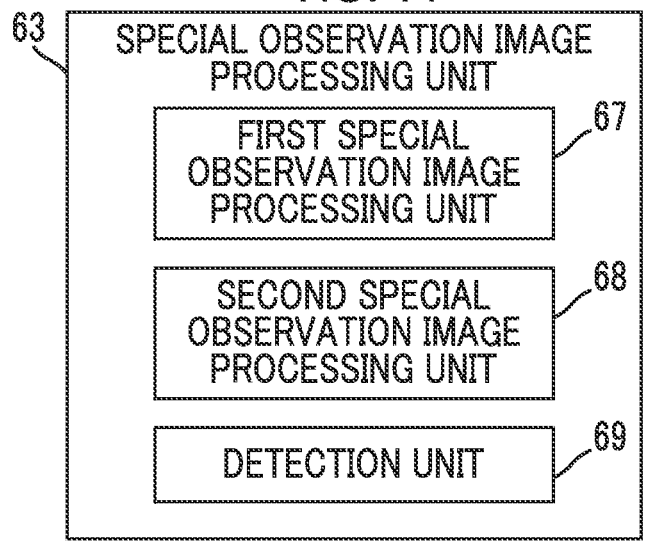
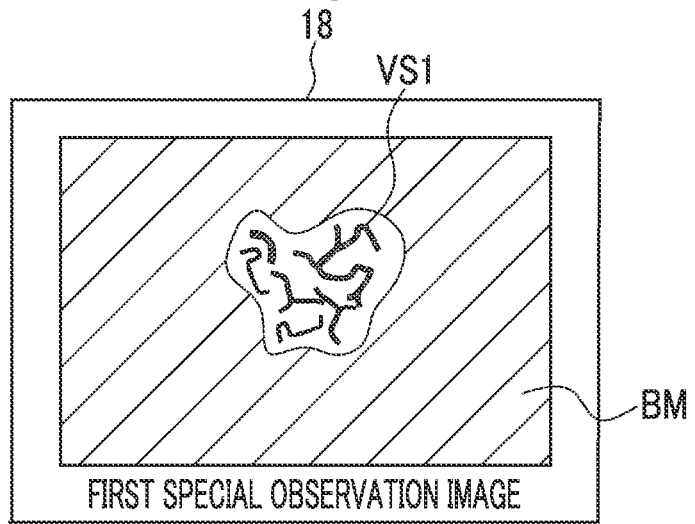

FIG. 13
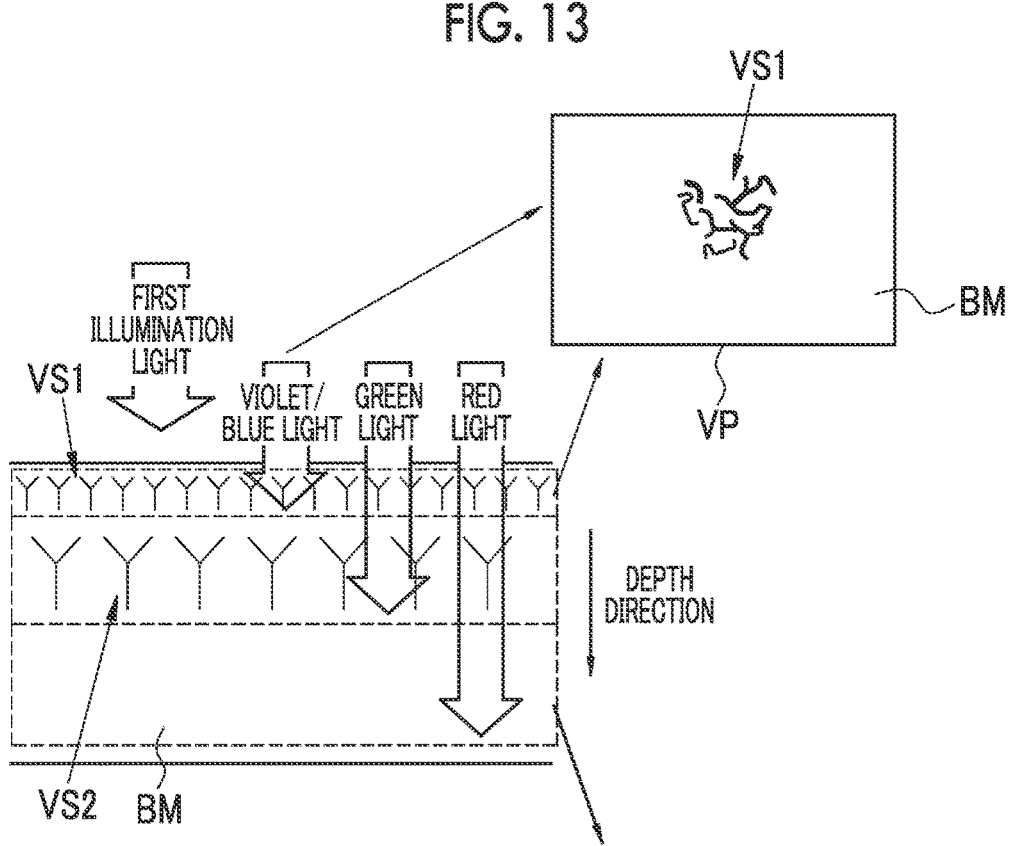
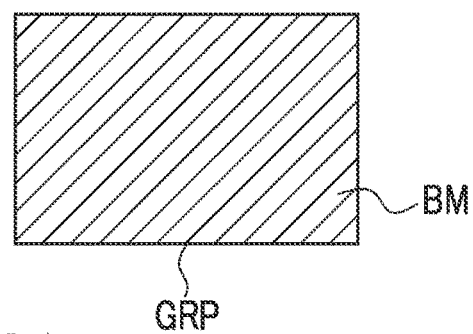
FIG. 14
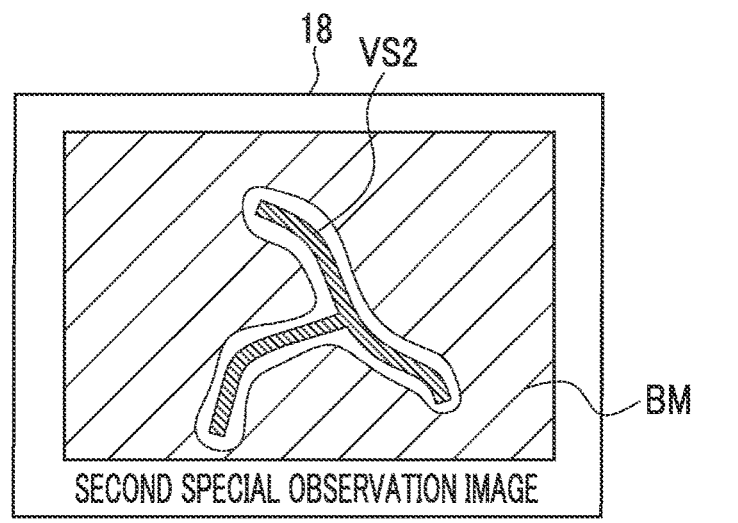

though the image of the subject to be observed is displayed on a monitor on the basis of RGB image signals that are obtained in a case where the image of the object to be observed, which is being illuminated with the illumination light, is picked up by an image pickup element of the endoscope.

ENDOSCOPE SYSTEM FOR CONTROLLING AN AMOUNT OF ILLUMINATION LIGHT

CROSS-REFERENCE TO RELATED APPLICATIONS

This application is a Continuation of PCT International Application No. PCT/JP2020/006020 filed on 17 Feb. 2020, which claims priority under 35 U.S.C § 119(a) to Japanese Patent Application No. 2019-027187 filed on 19 Feb. 2019. The above application is hereby expressly incorporated by reference, in its entirety, into the present application.

BACKGROUND OF THE INVENTION

1. Field of the Invention

The present invention relates to an endoscope system that switches and displays a plurality of kinds of images.

2. Description of the Related Art

In recent years, an endoscope system comprising a light source device, an endoscope, and a processor device has been widely used in a medical field. In the endoscope system, an object to be observed is irradiated with illumination light from an endoscope, and the image of the object to be observed is displayed on a monitor on the basis of RGB image signals that are obtained in a case where the image of the object to be observed, which is being illuminated with the illumination light, is picked up by an image pickup element of the endoscope.

In recent years, an object to be observed has been illuminated with a plurality of kinds of illumination light having wavelength ranges different from each other according to the purpose of diagnosis. For example, JP2015-173737A discloses that an object to be observed is alternately illuminated with two kinds of blue narrow-band light, that is, NB1 light having a peak wavelength of 422 nm and NB2 light having a peak wavelength in the range of 460 to 470 nm to acquire oxygen saturation in blood vessels included in the object to be observed. Further, WO2016/080130A (corresponding to US2017/0231502A1) discloses that an object to be observed is illuminated with light having a peak in a B1 region (first B region: 390 nm to 440 nm) and light having a peak in a B2 region (second B region: 440 nm to 490 nm) and the image of the object to be observed is picked up by an image pickup element including B-pixels having sensitivity to both light of the B1 region and light of the B2 region to obtain image information about superficial blood vessels. Furthermore, JP2017-185258A discloses that desired tissue information about biological tissue is acquired in a more clear state suitable for diagnosis using violet light having a central wavelength of 405 nm, blue laser light having a central wavelength of 445 nm, and the excitation emission of light excited and emitted by blue laser light.

SUMMARY OF THE INVENTION

In recent years, a diagnosis focusing on biological information other than a background mucous membrane, for example, blood vessels having different depths, glandular structures having different depths or heights, or the like has been made in an endoscopic field. A plurality of kinds of information other than the background mucous membrane need to be displayed in such a diagnosis so that a user can grasp the information. A method including illuminating an object with various kinds of light, which have different invasion depths to biological tissue and a plurality of wavelengths, while automatically and periodically switching the various kinds of light and switching and displaying a plurality of images obtained through the illumination of the various kinds of light is considered as a method of displaying the plurality of kinds of information, respectively. For example, in order to obtain information about a surface layer, such as superficial blood vessels, and information about a deep layer, such as deep blood vessels, a user illuminates an object with short-wavelength light having an invasion depth to a surface layer and medium-wavelength light having an invasion depth to a deep layer while switching the short-wavelength light and the medium-wavelength light, and switches and displays a surface layer image obtained through the illumination of the short-wavelength light and a deep layer image obtained through the illumination of the medium-wavelength light. Since a difference between the surface layer image and the deep layer image is displayed in a case where such switching display is performed, different biological information can be separated and displayed. Accordingly, a user can grasp biological information different from the surface layer information and the deep layer information.

In a case where a subject is illuminated with the various kinds of light having the respective wavelengths while the various kinds of light having the respective wavelengths are switched as described above, the amount of each of the various kinds of light having the respective wavelengths needs to be appropriately controlled according to the brightness of the subject. However, since spectral reflectivity is different from the spectral reflectivity of a standard subject due to the change of a subject, such as a difference in a portion to be observed, an individual difference, the presence or absence of diseases, such as inflammation, or the presence or absence of the spraying of dye, the brightness, tones, and the like of the respective images picked up using the various kinds of light having the plurality of wavelengths are significantly different from each other. In a case where a difference from a target brightness is significant during the switching of the various kinds of light having the respective wavelengths in this case, the amount of each of the various kinds of light having the respective wavelengths may not correspond to the brightness of the subject.

An object of the invention is to provide an endoscope system that can control the amount of each illumination light according to the change of a subject in a case where the subject is illuminated with a plurality of pieces of light while the plurality of pieces of light are switched.

An endoscope system according to an aspect of the invention comprises a light source unit that emits first illumination light and second illumination light having an emission spectrum different from an emission spectrum of the first illumination light, a first processor, and a second processor. In a case where the first processor performs control to automatically switch and emit the first illumination light and the second illumination light, each of a light emission period K(N) in which the first illumination light is emitted and a light emission period L(N) in which the second illumination light is emitted is a light emission period of at least one or more frames. The second processor acquires a first image signal group that includes first image signals obtained through image pickup of a subject illuminated with the first illumination light in the light emission period K(N) of the first illumination light and a second image signal group that includes second image signals obtained through image pickup of the subject illuminated with the second illumination light in the light emission period L(N) of the second illumination light, calculates a first brightness D1 of the subject from the first image signals, calculates a second brightness D2 of the subject from the second image signals, sets an amount of the first illumination light or the second illumination light on a basis of the first brightness or the second brightness, and performs at least one of adjustment of the amount of the second illumination light that is set at a first switching timing at which illumination light is switched to the second illumination light from the first illumination light or adjustment of the amount of the first illumination light that is set at a second switching timing at which illumination light is switched to the first illumination light from the second illumination light.

It is preferable that the second processor performs at least one of adjustment of an amount of the second illumination light, which is set at a first switching timing T1 of the light emission period L(N), using information about a first switching timing T1 of a light emission period L(N−2) before the light emission period L(N) or adjustment of an amount of the first illumination light, which is set at a second switching timing T2 of the light emission period K(N), using information about a second switching timing T2 of a light emission period K(N−2) before the light emission period K(N).

It is preferable that, in a case where N is set to 4 and an amount of the second illumination light set at a first switching timing T1 of a light emission period L(4) is to be adjusted, the amount of the second illumination light is multiplied by an adjustment factor X(2), which is obtained in a case where the target brightness is divided by a second brightness D2(2)* obtained at the first switching timing T1, as information about a first switching timing T1 of a light emission period L(2).

It is preferable that the second processor performs at least one of adjustment of an amount of the second illumination light, which is set at a first switching timing T1 of the light emission period L(N), using information about first switching timings T1 of a plurality of light emission periods L(N−P) before the light emission period L(N) or adjustment of an amount of the first illumination light, which is set at a second switching timing T2 of the light emission period K(N), using information about second switching timings T2 of light emission periods K(N−P) before the light emission period K(N).

It is preferable that a second brightness D2 obtained at the first switching timing T1 includes a plurality of second brightnesses D2(N−P) indicating second brightnesses obtained at the first switching timings T1 of the plurality of light emission periods L(N−P), respectively, and, in a case where the second processor adjusts the amount of the second illumination light set at the first switching timing T1 of the light emission period L(N), the amount of the second illumination light is multiplied by a specific adjustment factor X, which is obtained in a case where the target brightness is divided by a value of a sum of products of the plurality of second brightnesses D2(N−P) and weighting factors, as the information about the first switching timings T1 of the plurality of light emission periods L(N−P).

It is preferable that the second processor performs at least one of adjustment of an amount of the second illumination light, which is set at a first switching timing T1 of the light emission period L(N), using information about a second switching timing T2 of a light emission period K(N−1) before the light emission period L(N) or adjustment of an amount of the first illumination light, which is set at a second switching timing T2 of the light emission period K(N), using information about a first switching timing T1 of a light emission period L(N−1) before the light emission period K(N).

It is preferable that, in a case where N is set to 4 and an amount of the second illumination light set at a first switching timing T1 of a light emission period L(4) is to be adjusted, the amount of the second illumination light is multiplied by an adjustment factor Y(3), which is obtained in a case where the first brightness D1(3)* obtained at a second switching timing of a light emission period K(3) is divided by the target brightness, as the information about the second switching timing T2 of the light emission period K(3).

It is preferable that the second processor performs at least one of adjustment of an amount of the second illumination light, which is set at a first switching timing T1 of the light emission period L(N), using information about second switching timings T2 of a plurality of light emission periods K(N-Q) and first switching timings T1 of a plurality of light emission periods L(N-P) before the light emission period L(N) or adjustment of an amount of the first illumination light, which is set at a second switching timing T2 of the light emission period K(N), using information about first switching timings T1 of a plurality of light emission periods L(N-Q) and second switching timings T2 of a plurality of light emission periods K(N-P) before the light emission period K(N).

It is preferable that, in a case where N is set to 6 and the second processor adjusts an amount of the second illumination light set at a first switching timing T1 of a light emission period L(6), an amount of the second illumination light is multiplied by a specific adjustment factor Y based on a first brightness D1(5)* obtained at a second switching timing T2 of a light emission period K(5), a second brightness D2(4)* obtained at a first switching timing T1 of a light emission period L(4), and a preset target brightness V.

It is preferable that the first brightness or the second brightness is obtained on a basis of an average of pixel values of portions other than blood vessels or a lesion among the first image signals or the second image signals. It is preferable that the first brightness or the second brightness is obtained on a basis of an average of pixel values of pixels other than abnormal pixels, which include at least one of a dark portion or a halation, among the first image signals or the second image signals or on a basis of an average of pixel values of normal image signals other than the first image signals or the second image signals, which include the abnormal pixels, of the first image signal group or the second image signal group. It is preferable that the second processor adjusts the amount of the second illumination light or adjusts the amount of the first illumination light only in a case where the first brightness or the second brightness is in a predetermined target brightness range.

According to the invention, it is possible to control the amount of each illumination light according to the change of a subject in a case where the subject is illuminated with a plurality of pieces of light while the plurality of pieces of light are switched.

BRIEF DESCRIPTION OF THE DRAWINGS

FIG. 9 is a diagram illustrating the acquisition of a first image signal group and a second image signal group in time series.

FIG. 10 is a block diagram showing the functions of a DSP.

FIG. 11 is a block diagram showing the functions of a special image processing unit.

FIG. 12 is an image diagram showing a first special observation image.

FIG. 13 is a diagram illustrating a violet-blue light image and a green-red light image that are obtained in a case where a subject is illuminated with the first illumination light.

FIG. 14 is an image diagram showing a second special observation image.

DESCRIPTION OF THE PREFERRED EMBODIMENTS

First Embodiment

Figure 1:
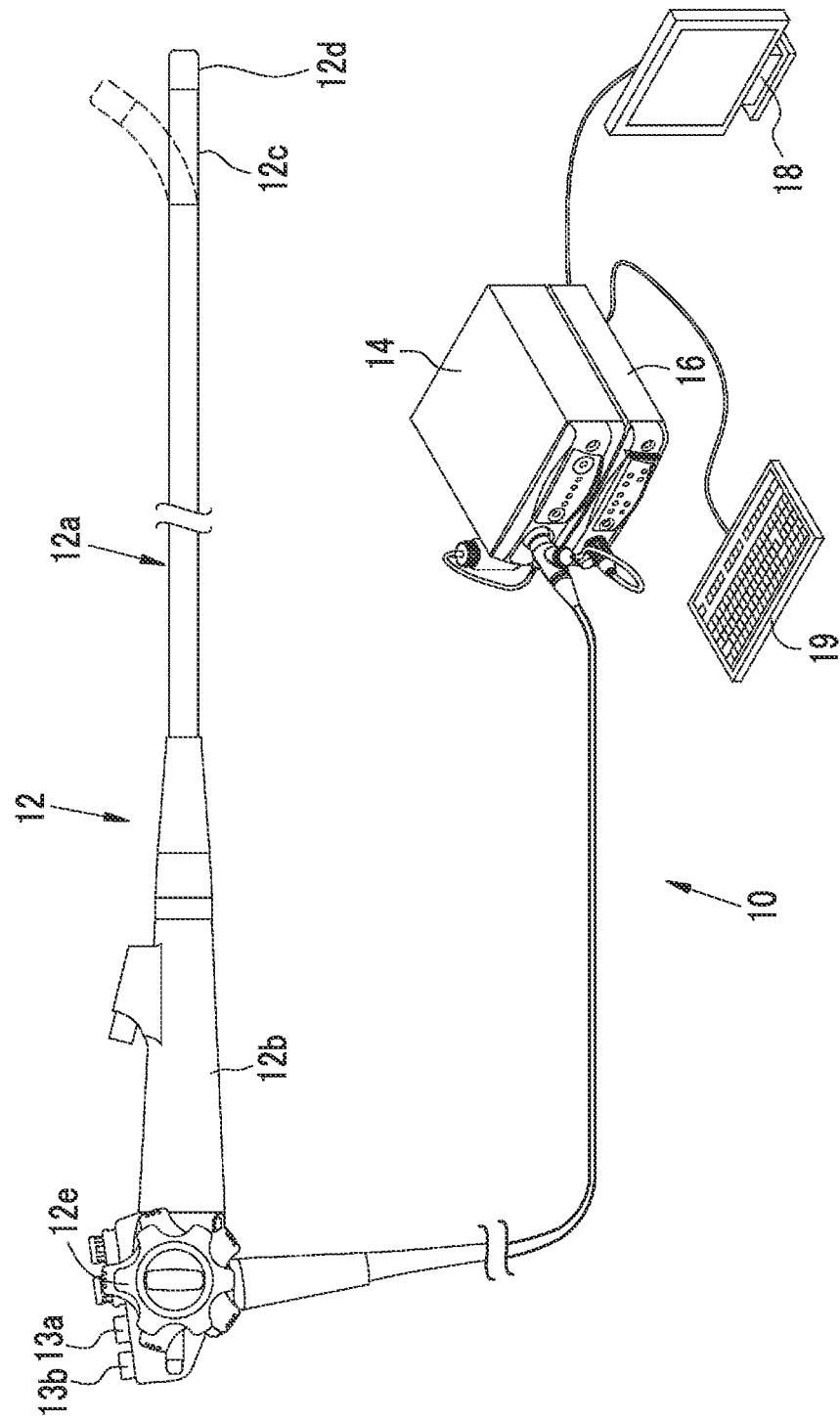
FIG. 1 is a diagram showing the appearance of an endoscope system according to a first embodiment.

As shown in FIG. 1, an endoscope system 10 according to a first embodiment includes an endoscope 12, a light source device 14, a processor device 16, a monitor 18 (display unit), and a user interface 19. The endoscope 12 is optically connected to the light source device 14, and is electrically connected to the processor device 16. The endoscope 12 includes an insertion part 12a that is to be inserted into an object to be examined, an operation part 12b that is provided at the proximal end portion of the insertion part 12a, and a bendable part 12c and a distal end part 12d that are provided on the distal end side of the insertion part 12a. In a case where angle knobs 12e of the operation part 12b are operated, the bendable part 12c is operated to be bent. As the bendable part 12c is operated to be bent, the distal end part 12d is made to face in a desired direction. The user interface 19 includes a mouse and the like in addition to a keyboard shown in FIG. 1.

Further, the operation part 12b is provided with a mode changeover SW 13a and a static image-acquisition instruction unit 13b in addition to the angle knobs 12e. The mode changeover SW 13a is used for an operation for switching a normal light observation mode, a first special light observation mode, a second special light observation mode, and a multi-observation mode. The normal light observation mode is a mode where a normal image is displayed on the monitor 18. The first special light observation mode is a mode where a first special observation image in which surface layer information, such as superficial blood vessels, is emphasized is displayed on the monitor 18. The second special light observation mode is a mode where a second special observation image in which deep layer information, such as deep blood vessels, is emphasized is displayed on the monitor 18. The multi-observation mode is a mode where the first special observation image (hereinafter, referred to as a first image) and the second special observation image (hereinafter, referred to as a second image) are automatically switched and displayed on the monitor 18. In order to switch a mode, a foot switch or the like may be used other than the mode changeover SW 13a.

The processor device 16 is electrically connected to the monitor 18 and the user interface 19. The monitor 18 outputs and displays image information and the like. The user interface 19 functions as a user interface (UI) that receives an input operation, such as function settings. An external recording unit (not shown), which records image information and the like, may be connected to the processor device 16.

Figure 2:
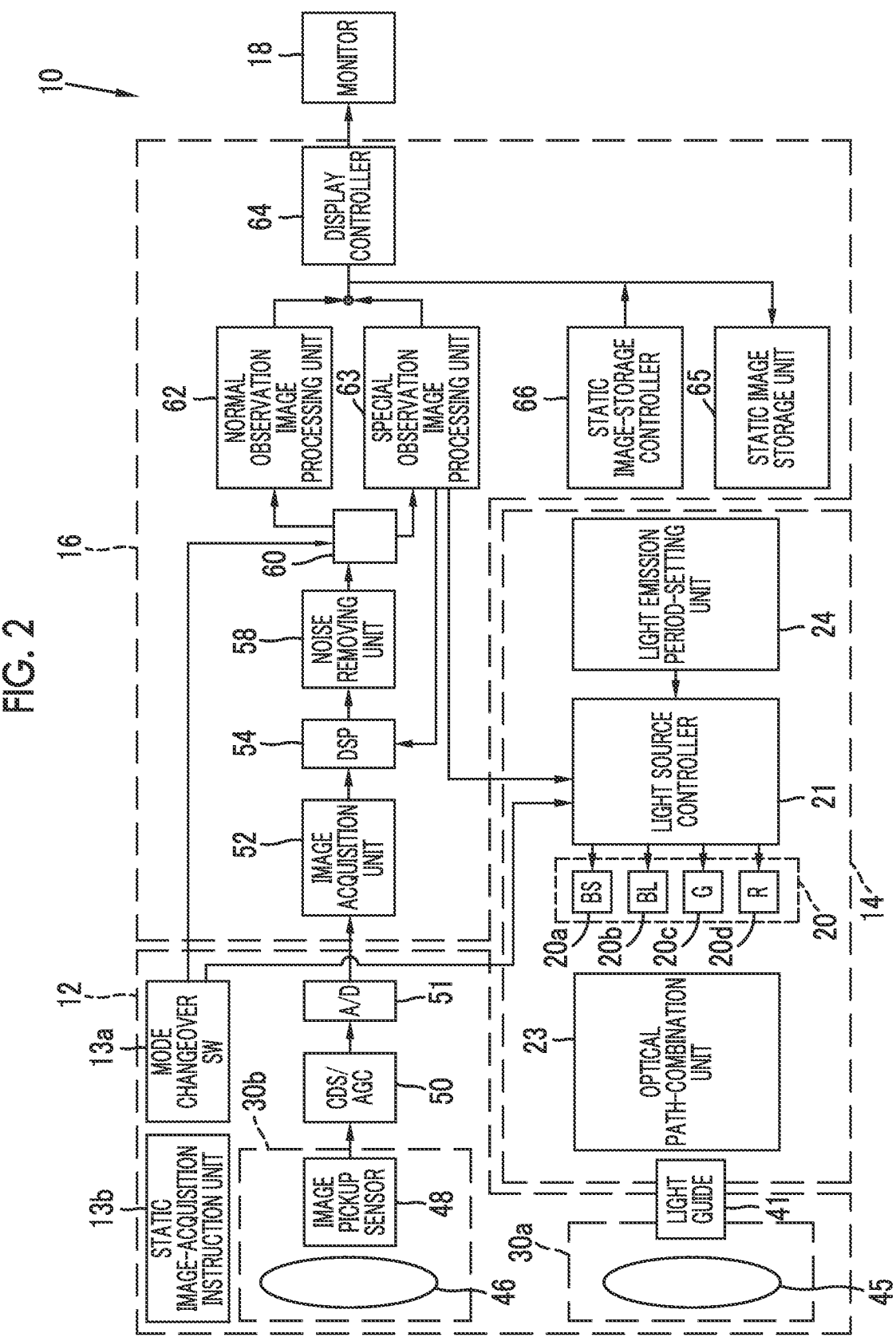
FIG. 2 is a block diagram showing the functions of the endoscope system according to the first embodiment.

As shown in FIG. 2, the light source device 14 includes a light source unit 20, a light source controller 21, an optical path-combination unit 23, and a light emission period-setting unit 24. The light source unit 20 includes a violet light emitting diode (V-LED) 20a, a blue light emitting diode (B-LED) 20b, a green light emitting diode (G-LED) 20c, and a red light emitting diode (R-LED) 20d. In the light source device 14, programs related to various kinds of control are stored in a program memory (not shown). The light source controller 21 formed of a first processor executes the programs stored in the program memory, so that the functions of the light source controller 21 are realized. Specifically, the light source controller 21 realizes a function to control the drive of the LEDs 20a to 20d. The optical path-combination unit 23 combines the optical paths of four kinds of color light that are emitted from the four color LEDs 20a to 20d. The inside of an object to be examined is irradiated with the pieces of light, which are combined by the optical path-combination unit 23, through a light guide 41 inserted into the insertion part 12a and an illumination lens 45. A laser diode (LD) may be used instead of the LED. The light emission period-setting unit 24 sets the light emission periods of a plurality of pieces of illumination light.

Figure 3:
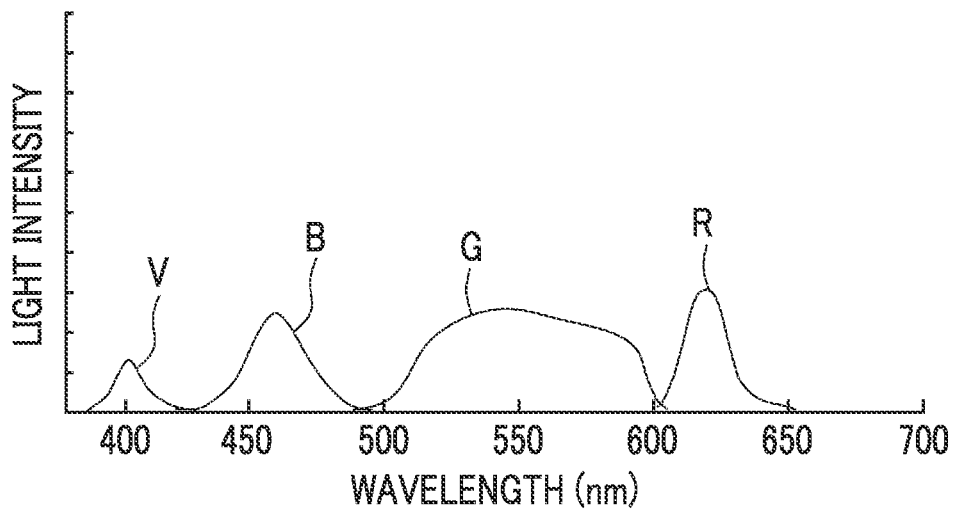
FIG. 3 is a graph showing the emission spectra of violet light V, blue light B, green light G, and red light R.

As shown in FIG. 3, the V-LED 20a generates violet light V of which the central wavelength is in the range of 405±10 nm and the wavelength range is in the range of 380 to 420 nm. The B-LED 20b generates blue light B of which the central wavelength is in the range of 460±10 nm and the wavelength range is in the range of 420 to 500 nm. The G-LED 20c generates green light G of which the wavelength range is in the range of 480 to 600 nm. The R-LED 20d generates red light R of which the central wavelength is in the range of 620 to 630 nm and the wavelength range is in the range of 600 to 650 nm.

The light source controller 21 controls the V-LED 20a, the B-LED 20b, the G-LED 20c, and the R-LED 20d. Further, the light source controller 21 controls the respective LEDs 20a to 20d so that normal light of which the light intensity ratios of violet light V, blue light B, green light G, and red light R are Vc:Bc:Gc:Rc is emitted in the normal light observation mode.

Figure 4:
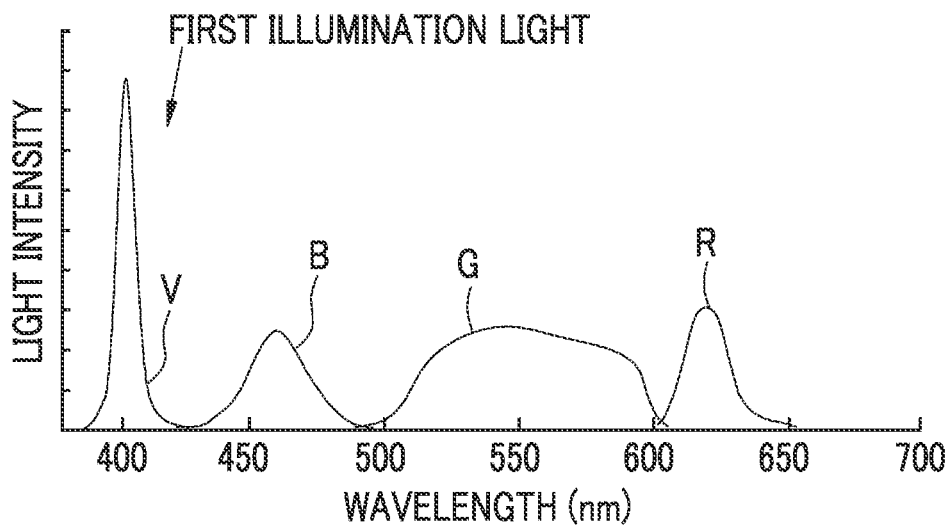
FIG. 4 is a graph showing the emission spectrum of first illumination light that includes violet light V, blue light B, green light G, and red light R.

Furthermore, the light source controller 21 controls the respective LEDs 20a to 20d so that first illumination light of which the light intensity ratios of violet light V, blue light B, green light G, and red light R are Vs1:Bs1:Gs1:Rs1 is emitted in the first special light observation mode. The light intensity ratios Vs1:Bs1:Gs1:Rs1 correspond to the light amount condition of the first illumination light. It is preferable that the first illumination light emphasizes superficial blood vessels. For this purpose, it is preferable that the light intensity of violet light V of the first illumination light is set to be higher than the light intensity of blue light B thereof. For example, as shown in FIG. 4, a ratio of the light intensity Vs1 of violet light V to the light intensity Bs1 of blue light B is set to "4:1".

In this specification, the light intensity ratios include a case where the ratio of at least one semiconductor light source is 0 (zero). Accordingly, the light intensity ratios include a case where any one or two or more of the respective semiconductor light sources are not turned on. For example, even though only one semiconductor light source is turned on and the other three semiconductor light sources are not turned on as in a case where the light intensity ratios of violet light V, blue light B, green light G, and red light R are 1:0:0:0, it is regarded that the light source unit 20 has light intensity ratios.

Figure 5:
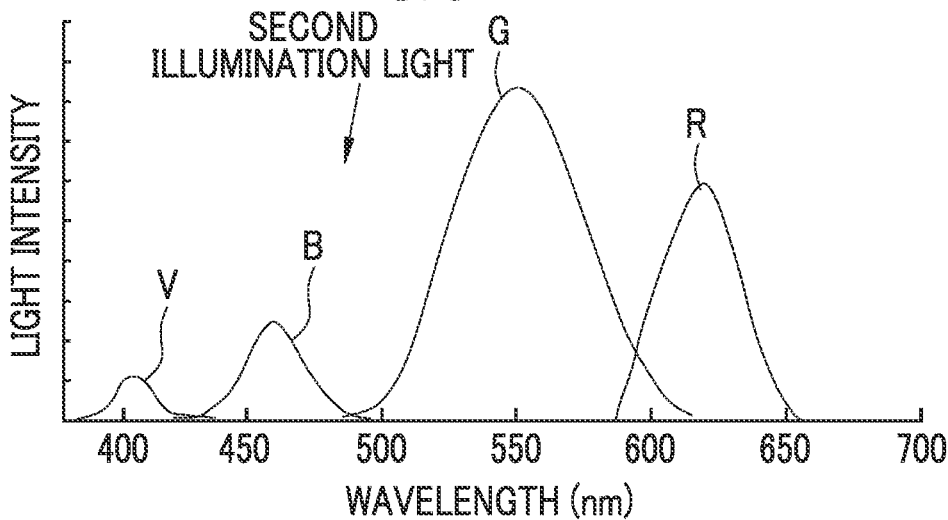
FIG. 5 is a graph showing the emission spectrum of second illumination light that includes violet light V, blue light B, green light G, and red light R.

Further, the light source controller 21 controls the respective LEDs 20a to 20d so that second illumination light of which the light intensity ratios of violet light V, blue light B, green light G, and red light R are Vs2:Bs2:Gs2:Rs2 is emitted in the second special light observation mode. The light intensity ratios Vs2:Bs2:Gs2:Rs2 correspond to the light amount condition of the second illumination light. It is preferable that the second illumination light emphasizes deep blood vessels. For this purpose, it is preferable that the light intensity of blue light B of the second illumination light is set to be higher than the light intensity of violet light V thereof. For example, it is preferable that a ratio of the light intensity Vs2 of violet light V to the light intensity Bs2 of blue light B is set to "1:3" as shown in FIG. 5.

In a case where a mode is set to the multi-observation mode, the light source controller 21 performs control to emit the first illumination light and the second illumination light for a light emission period K(N) and a light emission period L(N), respectively, and to automatically switch and emit the first illumination light and the second illumination light. Each of the light emission period K(N) and the light emission period L(N) has a light emission period of at least one or more frames. N is a natural number, and an increase in N means that processing is performed with time.

Figure 6:
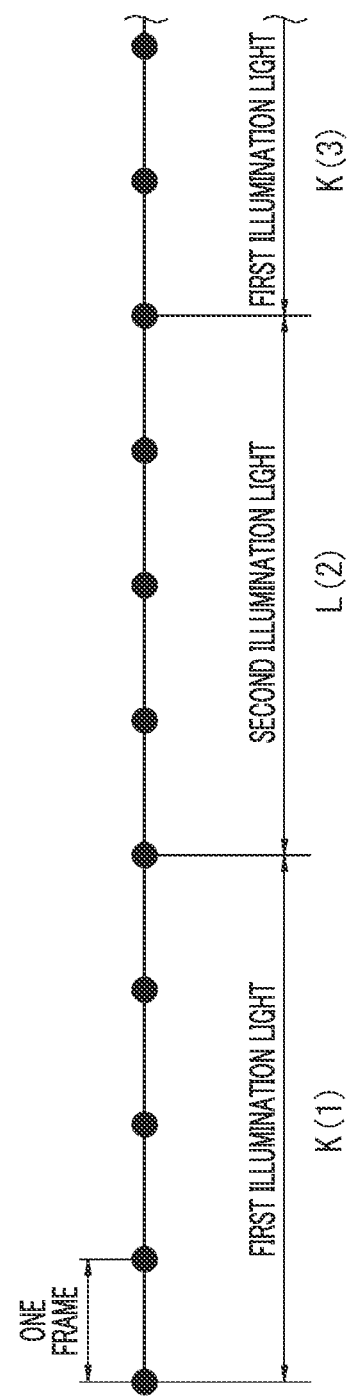
FIG. 6 is a diagram illustrating the light emission period of the first illumination light and the light emission period of the second illumination light.

More specifically, in a case where the light source controller 21 sets the light emission period K(N) to four frames and sets the light emission period L(N) to four frames, the second illumination light continues to be emitted for four frames in a light emission period L(2) after the first illumination light continues to be emitted for four frames in a light emission period K(1) as shown in, for example, FIG. 6. Then, this light emission pattern is repeated.

"Frame" means a unit used to control an image pickup sensor 48 (see FIG. 2) that picks up the image of an object to be observed. For example, "one frame" means a period including at least an exposure period where the image pickup sensor 48 is exposed to light emitted from an object to be observed and a read-out period where image signals are read out. In this embodiment, the light emission period K(N) or the light emission period L(N) is determined so as to correspond to "frame" that is a unit of image pickup.

Figure 7:
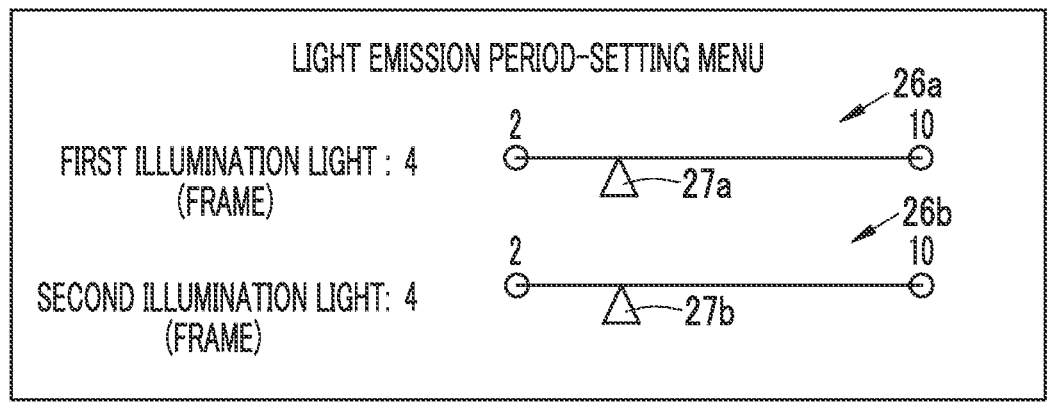
FIG. 7 is a diagram illustrating a light emission period-setting menu.

The light emission period K(N) and the light emission period L(N) can be appropriately changed by the light emission period-setting unit 24 that is connected to the light source controller 21. In a case where an operation for changing a light emission period is received by the operation of the user interface 19, the light emission period-setting unit 24 displays a light emission period-setting menu shown in FIG. 7 on the monitor 18. The light emission period K(N) can be changed between, for example, two frames and ten frames. Each light emission period is assigned to a slide bar 26a.

In a case where the light emission period K(N) is to be changed, a user operates the user interface 19 to position a slider 27a at a position on the slide bar 26a that represents a light emission period to which the user wants to change a light emission period. Accordingly, the light emission period K(N) is changed. Even in the case of the light emission period L(N), a user operates the user interface 19 to position a slider 27b at a position on a slide bar 26b (to which a light emission period in the range of, for example, two frames to ten frames is assigned) that represents a light emission period to which the user wants to change a light emission period. Accordingly, the light emission period L(N) is changed.

As shown in FIG. 2, the light guide 41 is built in the endoscope 12 and a universal cord (a cord connecting the endoscope 12 to the light source device 14 and the processor device 16), and transmits the pieces of light, which are combined by the optical path-combination unit 23, to the distal end part 12d of the endoscope 12. A multimode fiber can be used as the light guide 41. For example, a thin fiber cable of which a total diameter of a core diameter of 105 μm, a cladding diameter of 125 μm, and a protective layer forming a covering is in the range of φ0.3 to 0.5 mm can be used.

The distal end part 12d of the endoscope 12 is provided with an illumination optical system 30a and an image pickup optical system 30b. The illumination optical system 30a includes an illumination lens 45, and an object to be observed is irradiated with light transmitted from the light guide 41 through the illumination lens 45. The image pickup optical system 30b includes an objective lens 46 and an image pickup sensor 48. Light reflected from the object to be observed is incident on the image pickup sensor 48 through the objective lens 46. Accordingly, the reflected image of the object to be observed is formed on the image pickup sensor 48.

The image pickup sensor 48 is a color image pickup sensor, and picks up the reflected image of an object to be examined and outputs image signals. It is preferable that the image pickup sensor 48 is a charge coupled device (CCD) image pickup sensor, a complementary metal-oxide semiconductor (CMOS) image pickup sensor, or the like. The image pickup sensor 48 used in the embodiment of the present invention is a color image pickup sensor used to obtain RGB image signals corresponding to three colors of R (red), G (green), and B (blue), that is, a so-called RGB image pickup sensor that comprises R-pixels provided with R-filters, G-pixels provided with G-filters, and B-pixels provided with B-filters.

Figure 8:
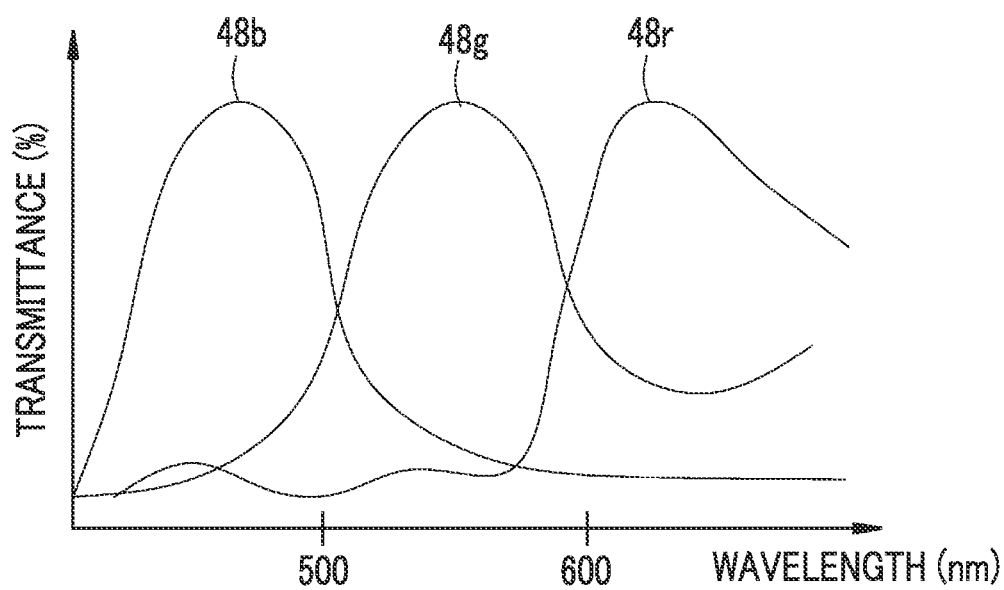
FIG. 8 shows the spectral transmittance of a B-filter, a G-filter, and an R-filter provided in an image pickup sensor.

As shown in FIG. 8, the B-filter 48*b* transmits light of a violet-light wavelength range, light of a blue-light wavelength range, and short-wavelength light of light of a green-light wavelength range. The G-filter 48*g* transmits light of a green-light wavelength range, long-wavelength light of light of a blue-light wavelength range, and short-wavelength light of light of a red-light wavelength range. The R-filter 48*r* transmits light of a red-light wavelength range and short-wavelength light of light of a green-light wavelength range. Accordingly, in the image pickup sensor 48, the B-pixel has sensitivity to violet light V and blue light B, the G-pixel has sensitivity to blue light B, green light G, and red light R, and the R-pixel has sensitivity to green light G and red light R.

The image pickup sensor 48 may be a so-called complementary color image pickup sensor, which comprises complementary color filters corresponding to C (cyan), M (magenta), Y (yellow), and G (green), instead of an RGB color image pickup sensor. In a case where a complementary color image pickup sensor is used, image signals corresponding to four colors of C, M, Y, and G are output. Accordingly, the image signals corresponding to four colors of C, M, Y, and G need to be converted into image signals corresponding to three colors of R, G, and B by complementary color-primary color conversion. Further, the image pickup sensor 48 may be a monochrome image pickup sensor that includes no color filter. In this case, since the light source controller 21 causes blue light B, green light G, and red light R to be emitted in a time-sharing manner, demosaicing needs to be added to processing for image pickup signals.

As shown in FIG. 2, the image signals output from the image pickup sensor 48 are transmitted to a CDS/AGC circuit 50. The CDS/AGC circuit 50 performs correlated double sampling (CDS) or auto gain control (AGC) on the image signals that are analog signals. The image signals, which have been transmitted through the CDS/AGC circuit 50, are converted into digital image signals by an analog/digital converter (A/D converter) 51. The digital image signals, which have been subjected to A/D conversion, are input to the processor device 16.

In the processor device 16, programs related to various kinds of processing or control are stored in a program memory (not shown). The programs stored in the program memory are executed by a central controller (not shown) provided in the processor device 16 formed of a second processor, so that the processor device 16 realizes the functions of an image acquisition unit 52, a digital signal processor (DSP) 54, a noise removing unit 58, a signal switching unit 60, a normal observation image processing unit 62, a special observation image processing unit 63, a display controller 64, a static image storage unit 65, and a static image-storage controller 66. As the programs are executed, the functions of a brightness calculation unit 55, a light amount-setting unit 56, and a set light amount-adjustment unit 57 to be described later included in the DSP 54 are also realized.

The image acquisition unit 52 acquires an observation image that is obtained in a case where the image of the object to be observed is picked up in the endoscope 12. Specifically, digital color image signals obtained from the endoscope 12 are input to the image acquisition unit 52 as an observation image. The color image signals are formed of red color signals output from the R-pixels of the image pickup sensor 48, green color signals output from the G-pixels of the image pickup sensor 48, and blue color signals output from the B-pixels of the image pickup sensor 48.

As shown in FIG. 9, the image acquisition unit 52 acquires a first image signal group in the light emission period K(N). The first image signal group includes a plurality of first image signals SP1 that are obtained in the light emission period K(N) from the image pickup of a subject illuminated with the first illumination light. Further, the image acquisition unit 52 acquires a second image signal group in the light emission period L(N). The second image signal group includes a plurality of second image signals SP2 that are obtained in the light emission period L(N) from the image pickup of the subject illuminated with the second illumination light. In a case where a mode is set to the multi-observation mode in this embodiment, the light source controller 21 performs control to emit the first illumination light and the second illumination light in the light emission period K(N) and the light emission period L(N), respectively, and to automatically switch and emit the first illumination light and the second illumination light. Accordingly, the image acquisition unit 52 periodically acquires images in the order of the first image signal group and the second image signal group over time.

Since each of the light emission period K(N) and the light emission period L(N) has a light emission period of at least one or more frames, the first image signal group and the second image signal group include at least one or more first image signals SP1 and at least one or more second image signals SP2, respectively. In this embodiment, each of the light emission period K(N) and the light emission period L(N) is a light emission period of four frames. Accordingly, the first image signal group including four first image signals SP1 is acquired in the light emission period K(N) and the second image signal group including four second image signals SP2 is acquired in the light emission period L(N).

The DSP 54 performs various kinds of signal processing, such as defect correction processing, offset processing, white balance processing, linear matrix processing, gamma conversion processing, and demosaicing processing, on the received image signals. Further, the DSP 54 comprises a brightness calculation unit 55, a light amount-setting unit 56, and a set light amount-adjustment unit 57 as shown in FIG. 10. Information about the amount of normal light and the amount of the first or second illumination light obtained from the light amount-setting unit 56 or the set light amount-adjustment unit 57 is sent to the light source controller 21. The light source controller 21 controls the amount of normal light and the amount of the first or second illumination light on the basis of the information about the amount of light obtained from the light amount-setting unit 56 or the set light amount-adjustment unit 57. The details of the brightness calculation unit 55, the light amount-setting unit 56, and the set light amount-adjustment unit 57 will be described later.

Signals of defective pixels of the image pickup sensor 48 are corrected in the defect correction processing. Dark current components are removed from the image signals having been subjected to the defect correction processing in the offset processing, so that an accurate zero level is set. The first image signals are multiplied by a first gain factor and the second image signals are multiplied by a second gain factor, so that white balance processing is performed. The image signals having been subjected to the offset processing are multiplied by a gain in the white balance processing, so that signal levels are adjusted. The linear matrix processing for improving color reproducibility is performed on the image signals having been subjected to the white balance processing. After that, a brightness or a saturation is adjusted by the gamma conversion processing. The demosaicing processing (also referred to as equalization processing or demosaicing) is performed on the image signals having been subjected to the linear matrix processing, so that signals of colors deficient in the respective pixels are generated by interpolation. All the pixels are made to have the signals of the respective colors by this demosaicing processing.

The noise removing unit 58 performs noise removal processing (for example, a moving-average method, median filtering, or the like) on the image signals, which have been subjected to gamma correction and the like by the DSP 54, to remove noise from the image signals. The image signals from which noise has been removed are transmitted to the signal switching unit 60.

In a case where a mode is set to the normal light observation mode by the mode changeover SW 13a, the signal switching unit 60 transmits image signals for normal light, which are obtained through the illumination of normal light and image pickup, to the normal observation image processing unit 62. As shown in FIG. 11, the special observation image processing unit 63 includes a first special observation image processing unit 67, a second special observation image processing unit 68, and a detection unit 69. Further, in a case where a mode is set to the first special light observation mode, the signal switching unit 60 transmits first image signals, which are obtained through the illumination of the first illumination light and image pickup, to the first special observation image processing unit 67. The first image signals include first red color signals that are output from the R-pixels of the image pickup sensor, first green color signals that are output from the G-pixels of the image pickup sensor 48, and first blue color signals that are output from the B-pixels of the image pickup sensor 48. Furthermore, in a case where a mode is set to the second special light observation mode, the signal switching unit 60 transmits second image signals, which are obtained through the illumination of the second illumination light and image pickup, to the second special observation image processing unit 63. The second image signals include second red color signals that are output from the R-pixels of the image pickup sensor, second green color signals that are output from the G-pixels of the image pickup sensor 48, and second blue color signals that are output from the B-pixels of the image pickup sensor 48. Moreover, in a case where a mode is set to the multi-observation mode, first image signals obtained through the illumination of the first illumination light and image pickup are transmitted to the first special observation image processing unit 67 and second image signals obtained through the illumination of the second illumination light and image pickup are transmitted to the second special observation image processing unit 63.

The normal observation image processing unit 62 performs image processing for a normal image on the RGB image signals that are obtained in the normal light observation mode. The image processing for a normal image includes structure emphasis processing for a normal image and the like. The normal observation image processing unit 62 includes parameters for a normal image, which are to be multiplied by the RGB image signals, to perform the image processing for a normal image. The RGB image signals having been subjected to the image processing for a normal image are input to the display controller 64 from the normal observation image processing unit 62 as a normal image.

The first special observation image processing unit 67 generates a first image having been subjected to image processing, such as saturation emphasis processing, hue emphasis processing, and structure emphasis processing, on the basis of the first image signals. In the first image, many superficial blood vessels are included and the color of the background mucous membrane is also accurately reproduced. The first special observation image processing unit 67 includes parameters for a first image, which are to be multiplied by the first image signals, to perform the image processing for a first image. The first special observation image processing unit 67 does not perform superficial blood vessel emphasis processing for emphasizing superficial blood vessels, but may perform the superficial blood vessel emphasis processing depending on the situation of a processing load.

An image in which a background mucous membrane BM and superficial blood vessels VS1 of an object to be observed are shown as shown in FIG. 12 is displayed by the first image. The first image is obtained on the basis of the first illumination light that includes violet light, blue light, green light, and red light. In a case where the object to be observed is illuminated with the first illumination light, violet light V and blue light B of the first illumination light reach a surface layer where the superficial blood vessels VS1 are distributed as shown in FIG. 13. Accordingly, the image of the superficial blood vessels VS1 is included in a violet light image VP obtained on the basis of the reflected light of violet light V and blue light B. Here, since the light intensity of violet light V is higher than the light intensity of blue light B, an image obtained on the basis of the reflected light of violet light V and blue light B is referred to as a violet light image VP. Further, green light G and red light R of the first illumination light reach the background mucous membrane BM that is distributed at a position deeper than the superficial blood vessels VS1 and the deep blood vessels VS2 (blood vessels present at positions deeper than the superficial blood vessels VS1). Accordingly, the image of the background mucous membrane BM is included in a green-red light image GRP that is obtained on the basis of the reflected light of green light G and red light R. Since the first image is an image in which the violet light image VP and the green-red light image GRP are combined with each other as described above, the images of the background mucous membrane BM and the superficial blood vessels VS1 are displayed.

The second special observation image processing unit 68 generates a second image having been subjected to image processing, such as saturation emphasis processing, hue emphasis processing, and structure emphasis processing, on the basis of the second image signals. In the second image, many deep blood vessels are included and the color of the background mucous membrane is also accurately reproduced. The second special observation image processing unit 68 includes parameters for a second image, which are to be multiplied by the second image signals, to perform the image processing for a second image. The second special observation image processing unit 68 does not perform deep blood vessel emphasis processing for emphasizing deep blood vessels, but may perform the deep blood vessel emphasis processing depending on the situation of a processing load.

Figure 15:
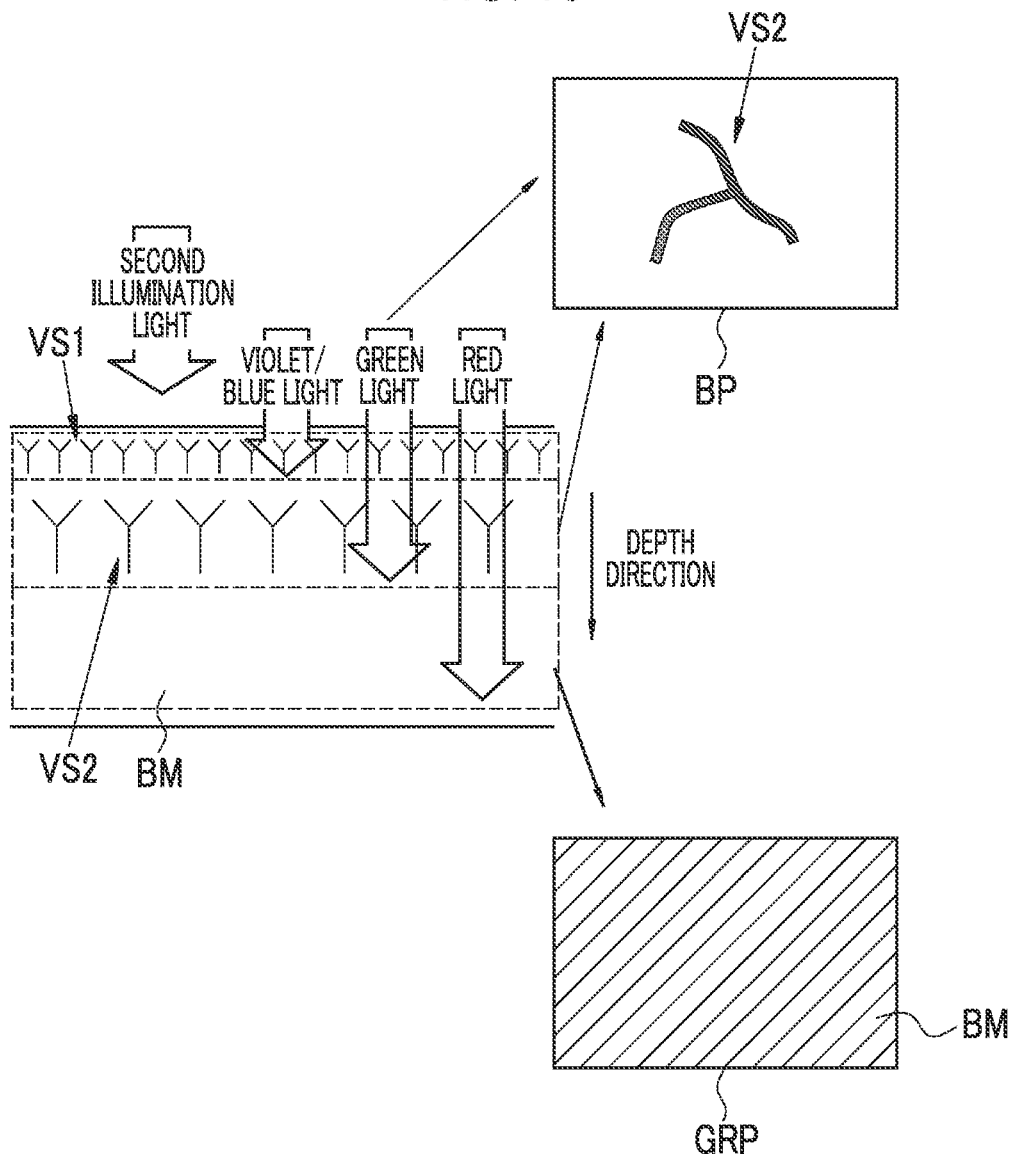
FIG. 15 is a diagram illustrating a violet-blue light image and a green-red light image that are obtained in a case where a subject is illuminated with the second illumination light.

An image in which the background mucous membrane BM and the deep blood vessels VS2 of the object to be observed are shown as shown in FIG. 14 is displayed by the second image. The second image is obtained on the basis of the second illumination light that includes violet light, blue light, green light, and red light. In a case where the object to be observed is illuminated with the second illumination light, violet light V and blue light B of the second illumination light reach a deep layer where the deep blood vessels VS2 are distributed as shown in FIG. 15. Accordingly, the image of the deep blood vessels VS2 is included in a blue light image BP obtained on the basis of the reflected light of violet light V and blue light B. Here, since the light intensity of blue light B is higher than the light intensity of violet light V, an image obtained on the basis of the reflected light of violet light V and blue light B is referred to as a blue light image BP. Further, green light G and red light R of the second illumination light reach the background mucous membrane BM that is distributed at a position deeper than the superficial blood vessels VS1 and the deep blood vessels VS2 (blood vessels present at positions deeper than the superficial blood vessels VS1). Accordingly, the image of the background mucous membrane BM is included in a green-red light image GRP that is obtained on the basis of the reflected light of green light G and red light R. Since the second image is an image in which the blue light image BP and the green-red light image GRP are combined with each other as described above, the images of the background mucous membrane BM and the deep blood vessels VS2 are displayed.

As described above, in this embodiment, it is preferable that the first special observation image is generated by the first image signals, the second special observation image is generated by the second image signals, the superficial blood vessels are emphasized in the first special observation image, and medium-deep blood vessels present at positions deeper than the superficial blood vessels are emphasized in the second special observation image.

The detection unit 69 detects blood vessels or a lesion by the normal image, the first image, and the second image. Since the first image is an image in which the superficial blood vessels VS1 are shown, and the second image is an image in which the deep blood vessels VS2 are shown as described above, these blood vessels can be detected by image processing. Further, blood vessels or a lesion may be detected using a normal observation image in addition to the first and second images by the image processing of these images. Furthermore, the detection unit 69 detects an abnormal portion of the first or second image, and regards the detected abnormal portion as abnormal image signals. The detection results of the blood vessels or the lesion are sent to the DSP 54 or the light source controller 21.

The display controller 64 performs control to display the normal image, the first image, and/or the second image, which are input from the normal observation image processing unit 62 or the special observation image processing unit 63, as images that can be displayed on the monitor 18. An image corresponding to each observation mode is displayed by the control of the display controller 64. In the case of the normal light observation mode, the normal image is displayed on the monitor 18. Further, the first image (see FIG. 12) is displayed on the monitor 18 in the case of the first special light observation mode. Furthermore, the second image (see FIG. 14) is displayed on the monitor 18 in the case of the second special light observation mode.

Moreover, in the case of the multi-observation mode, the first image and the second image, which are color images, are switched and displayed on the monitor 18 according to the light emission period of the first illumination light and the light emission period of the second illumination light. That is, in a case where the light emission period K(N) is four frames and the light emission period L(N) is four frames, the first special observation image continues to be displayed for four frames and the second special observation image continues to be displayed for four frames.

As described above, two kinds of the first and second images can be automatically switched and displayed in the multi-observation mode without the operation of the mode changeover SW 13a that is performed by a user. Since the first and second images are automatically switched and displayed in this way, the same object to be observed is displayed in the first and second images as long as the object to be observed is not moved or the distal end part 12d of the endoscope 12 is not moved. However, since the spectral information of the first image and the spectral information of the second image are different from each other even in the case of the same object to be observed, the object to be observed looks different depending on a difference in spectral information. That is, the visibility of the superficial blood vessels is high in the first image, but the visibility of the deep blood vessels is high in the second image. Accordingly, since the first and second images are switched and displayed, the visibility of a plurality of blood vessels having different depths can be improved.

As shown in FIG. 2, the static image-storage controller 66 performs control to store an image, which is obtained according to the instruction of the static image-acquisition instruction unit 13b at the timing of a static image-acquisition instruction, in the static image storage unit 65 as a static image. In the case of the normal light observation mode, the static image-storage controller 66 stores a normal image, which is obtained at the timing of the static image-acquisition instruction, in the static image storage unit 65 as a static image. In the case of the first special light observation mode, the static image-storage controller 66 stores a first special observation image, which is obtained at the timing of the static image-acquisition instruction, in the static image storage unit 65 as a static image. In the case of the second special light observation mode, the static image-storage controller 66 stores a second special observation image, which is obtained at the timing of the static image-acquisition instruction, in the static image storage unit 65 as a static image. Further, in the case of the multi-observation mode, the static image-storage controller 66 stores a set of observation images for display, which is formed of the first special observation image and the second special observation image obtained at the timing of the static image-acquisition instruction, in the static image storage unit 65.

The details of the brightness calculation unit 55, the light amount-setting unit 56, and the set light amount-adjustment unit 57 will be described below. In the case of the normal light observation mode, the brightness calculation unit 55 calculates the brightness of a subject from the image signals that are obtained in the normal light observation mode. The light amount-setting unit 56 sets the amount of normal light on the basis of the calculated brightness of the subject. The light source controller 21 controls the amount of normal light on the basis of the amount of normal light that is set by the light amount-setting unit 56.

In the case of the first special light observation mode, the brightness calculation unit 55 calculates a first brightness D1 of the subject from the first image signals. The light amount-setting unit 56 sets the amount of first illumination light from the first brightness D1. Then, the light source controller 21 controls the amount of first illumination light on the basis of the amount of first illumination light that is set by the light amount-setting unit 56. In the case of the second special light observation mode, the brightness calculation unit 55 calculates second brightness D2 of the subject from the second image signals. The light amount-setting unit 56 sets the amount of second illumination light from the second brightness D2. Then, the light source controller 21 controls the amount of second illumination light on the basis of the amount of second illumination light that is set by the light amount-setting unit 56.

The brightness calculation unit 55 may obtain the first brightness D1 or the second brightness D2 on the basis of the average of pixel values of portions other than blood vessels or a lesion among the first image signals or the second image signals, in addition to obtaining the first brightness D1 or the second brightness D2 using the pixel values of all pixels of the first image signals or the second image signals. Further, the first brightness D1 or the second brightness D2 may be obtained from an average of the pixel values of pixels other than abnormal pixels, which include at least one of dark portions or halations, among the first image signals or the second image signals. Furthermore, the first brightness D1 or the second brightness D2 may be obtained on the basis of an average of the pixel values of normal image signals other than the first image signals or the second image signals, which include abnormal pixels, of the first image signal group or the second image signal group.

Figure 16:
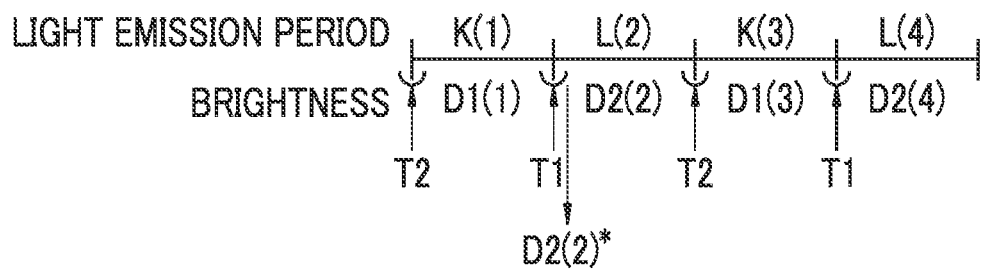
FIG. 16 is a diagram illustrating a light emission period and a brightness that show a second brightness D2(2)* used to adjust the amount of the second illumination light.

In a case where the first illumination light is emitted in a light emission period K(1) and a light emission period K(3) of the first illumination light as shown in FIG. 16 in the multi-observation mode, a first brightness D1(1) and a first brightness D2(3) are calculated from the first image signals and the amount of the first illumination light is set on the basis of the first brightness D1(1) and the first brightness D2(3) as in the first special light observation mode. Further, in a case where the second illumination light is emitted in a light emission period L(2) and a light emission period L(4) of the second illumination light, a second brightness D2(2) and a second brightness D2(4) are calculated from the second image signals and the amount of the second illumination light is set on the basis of the second brightness D2(2) and the second brightness D2(4) as in the second special light observation mode.

On the other hand, the set light amount-adjustment unit 57 adjusts the amount of the second illumination light that is set at a first switching timing T1 at which illumination light is switched to the second illumination light from the first illumination light. Likewise, the set light amount-adjustment unit 57 adjusts the amount of the first illumination light that is set at a second switching timing T2 at which illumination light is switched to the first illumination light from the second illumination light.

In the first embodiment, the amount of the second illumination light, which is set at a first switching timing T1 of the light emission period L(N), is adjusted using information about a first switching timing T1 of a light emission period L(N−2) before the light emission period L(N), or the amount of the first illumination light, which is set at a second switching timing T2 of the light emission period K(N), is adjusted using information about a second switching timing T2 of a light emission period K(N−2) before the light emission period K(N).

Specifically, the set light amount-adjustment unit 57 adjusts the amount of the second illumination light, which is set at a first switching timing T1 of the light emission period L(4), using information about a first switching timing T1 of the light emission period L(2) before the light emission period L(4), or adjusts the amount of the first illumination light, which is set at a second switching timing T2 of the light emission period K(3), using information about a second switching timing T2 of the light emission period K(1) before the light emission period K(3).

The first switching timing T1 is included in both the light emission period K(N) of the first illumination light and a light emission period L(N+1) of the second illumination light, and corresponds to both the light emission timing of the last frame of the light emission period K(3) and the light emission timing of the first frame of the light emission period L(4) in the case of, for example, FIG. 16. The second switching timing T2 is included in both the light emission period L(N) of the second illumination light and a light emission period K(N+1) of the first illumination light, and corresponds to both the light emission timing of the last frame of the light emission period L(2) and the light emission timing of the first frame of the light emission period K(3) in the case of, for example, FIG. 16.

For example, in a case where the amount of the second illumination light set by the light amount-setting unit 56 is to be adjusted at the first switching timing T1 of the light emission period L(4) of the second illumination light, the amount of light is adjusted using an adjustment factor X(2) that is based on a second brightness D2(2)* obtained at the first switching timing T1 of the light emission period L(2) before the light emission period L(4) and a preset target brightness V.

It is preferable that the adjustment factor X(2) is obtained in a case where the target brightness V is divided by the second brightness D2(2)* (adjustment factor X(2)=V/D2(2)*). That is, in a case where the amount of the second illumination light set at the first switching timing T1 of the light emission period L(4) is defined as the amount H2(4) of light, the amount H2(4)* of the second illumination light having been subjected to the adjustment of the amount of light is obtained from the product of the adjustment factor X(2) and the amount H2(4) of light (H2(4)*=X(2)×H2(4)). The amount H2(4)* of the second illumination light having been subjected to the adjustment of the amount of light is sent to the light source controller 21, and the light source controller 21 controls the amount of the second illumination light on the basis of the amount H2(4)* of the second illumination light having been subjected to the adjustment of the amount of light.

Figure 17:
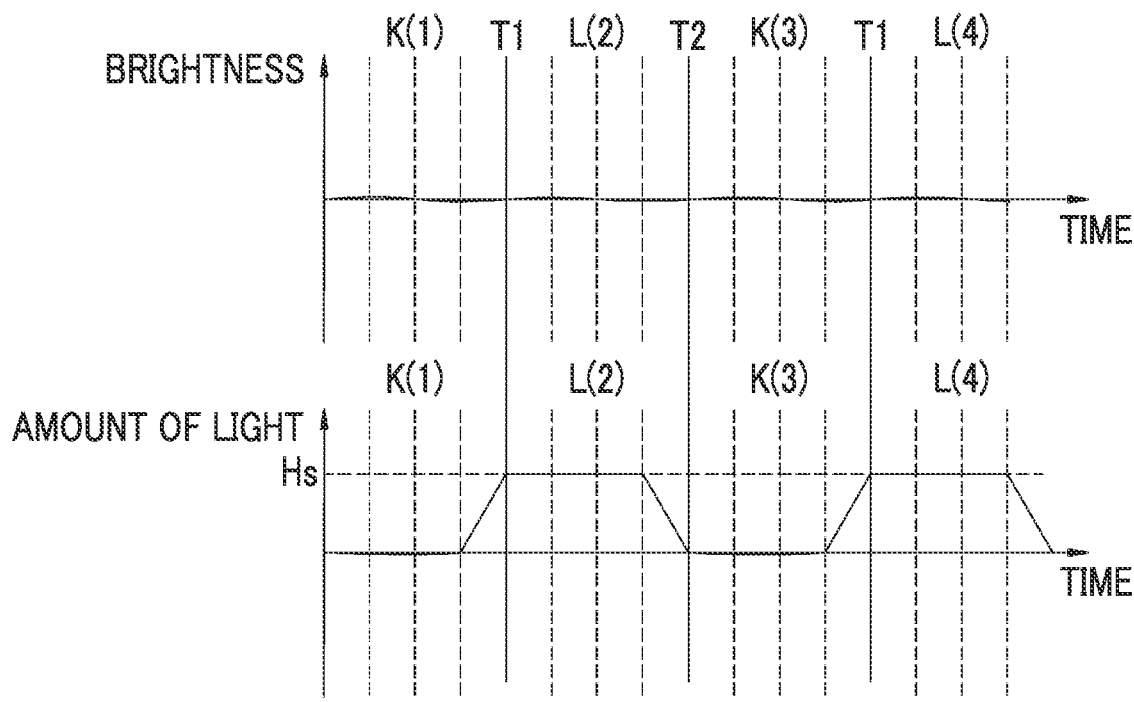
FIG. 17 is a diagram illustrating a relationship between a brightness and the amount of light in a case where a subject is standard.

Since the amount of the second illumination light is adjusted using the adjustment factor X as described above, the amount of light appropriate can be controlled according to the brightness of a subject even in a case where the subject is not standard, such as a case where portions to be observed are different from each other, a case where portions to be observed have individual differences, and portions to be observed have diseases, such as inflammation. For example, in a case where a subject is standard, the amount of the second illumination light is increased to a light amount value Hs by auto exposure (AE) control, which is performed by the light source controller 21, as shown in FIG. 17 as illumination light is switched to the second illumination light from the first illumination light. As a result, a brightness in the light emission period K(1) of the first illumination light and a brightness in the light emission period L(2) of the second illumination light can be made to be substantially equal to each other.

Figure 18:
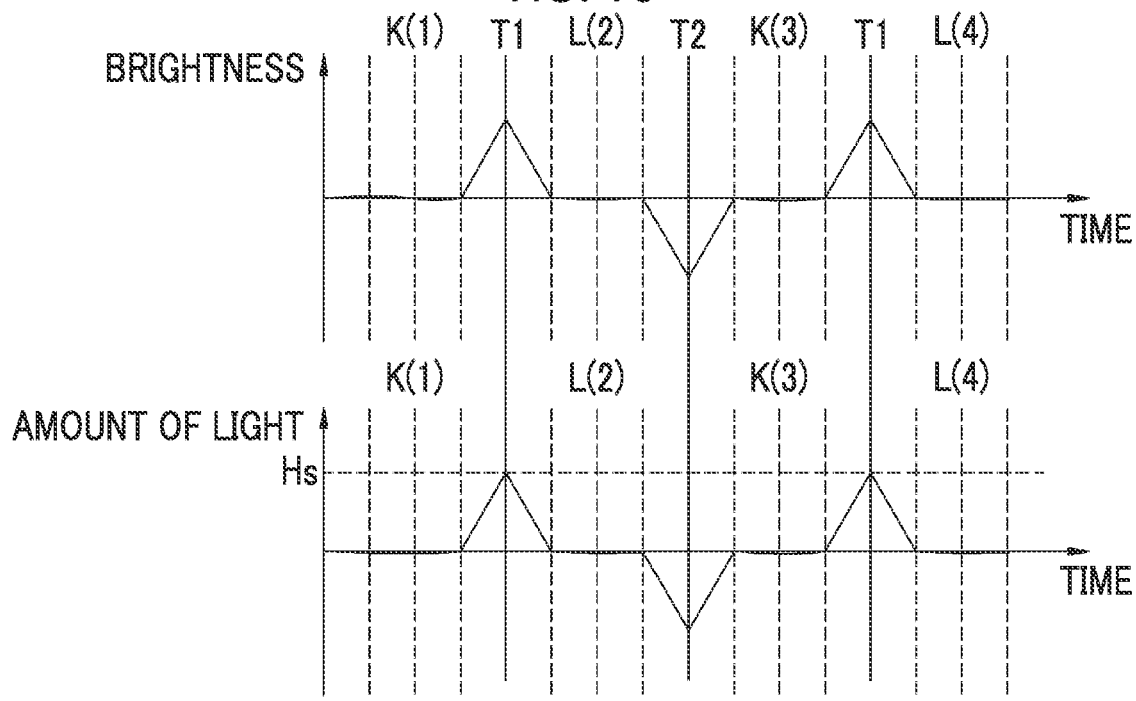
FIG. 18 is a diagram illustrating a relationship between a brightness and the amount of light in a case where a subject is not standard.

On the other hand, in a case where a subject is not standard, for example, the reflectivity of a subject for green light is high and the amount of the second illumination light is increased to a light amount value Hs by auto exposure (AE) control, which is performed by the light source controller 21, as shown in FIG. 18 as illumination light is switched to the second illumination light from the first illumination light, a brightness fluctuates at the first switching timing T1 at which a light emission period is switched to the light emission period L(2) from the light emission period K(1) in a case where the adjustment of the amount of the second illumination light using information about the first switching timing T1 (adjustment factor X(2)) as in this embodiment is not performed. This can occur since the reflectivity of a subject in a green-light wavelength range is high unlike a standard subject. However, after the first frame in the light emission period L(2), a brightness converges to an appropriate brightness due to AE control. The above-mentioned fluctuation in brightness may occur even at the second switching timing T2 at which a light emission period is switched to the light emission period K(3) from the light emission period L(2).

Figure 19:
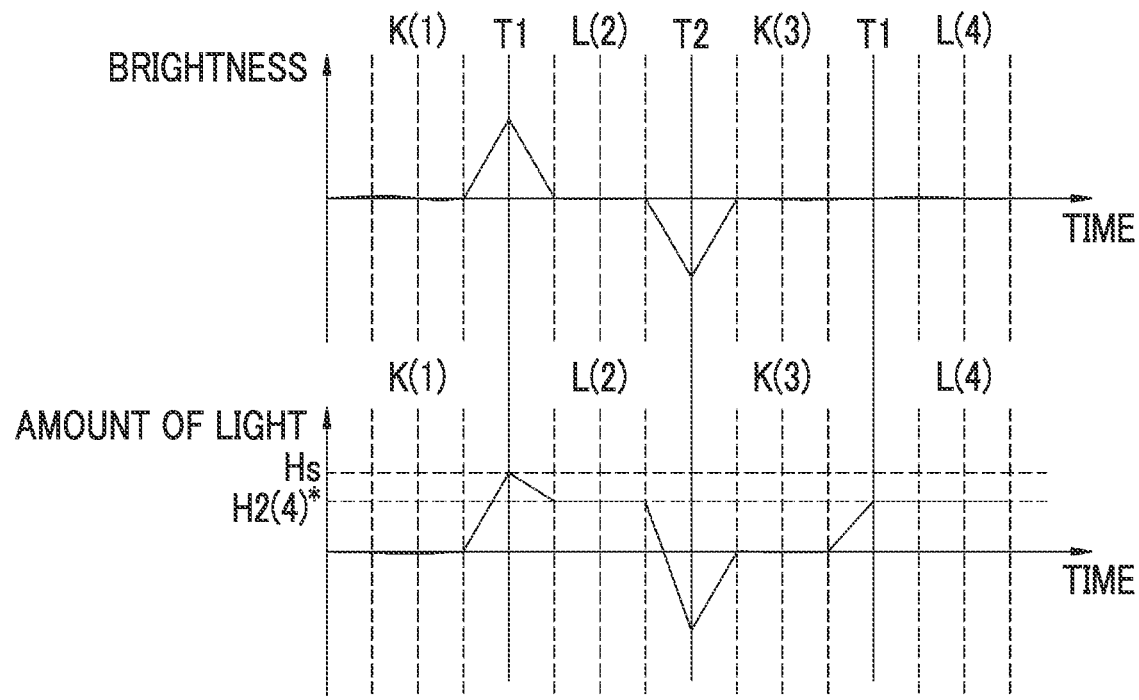
FIG. 19 is a diagram illustrating a relationship between a brightness and the amount of light in a case where a subject is not standard and the amount of light is adjusted.

Accordingly, in order to suppress a fluctuation in the amount of light at the first switching timing T1 or the second switching timing T2 in a case where a subject is not standard, the amount of the second illumination light is adjusted using information about the first switching timing T1 (adjustment factor X(2)) in the light emission period L(4) as shown in FIG. 19. Then, the subject is illuminated with the second illumination light on the basis of the amount H2(4)* of light having been subjected to the adjustment of the amount of light, so that a fluctuation in the amount of light at the first switching timing T1 can be suppressed and a brightness in the light emission period K(3) and a brightness in the light emission period L(4) can be made to be substantially equal to each other.

Further, the amount of the second illumination light set at the first switching timing T1 of the light emission period L(N) may be adjusted using information about first switching timings T1 of a plurality of light emission periods L(N-P) before the light emission period L(N), or the amount of the first illumination light set at the second switching timing T2 of the light emission period K(N) may be adjusted using information about second switching timings T2 of light emission periods K(N-P) before the light emission period K(N). P is an even number smaller than N.

Figure 20:
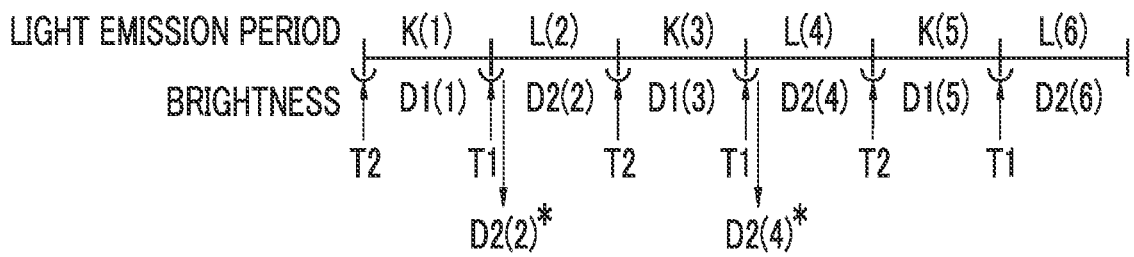
FIG. 20 is a diagram illustrating a light emission period and a brightness that show a second brightness D2(2)* and a second brightness D2(4)* used to adjust the amount of the second illumination light.
Figure 21:
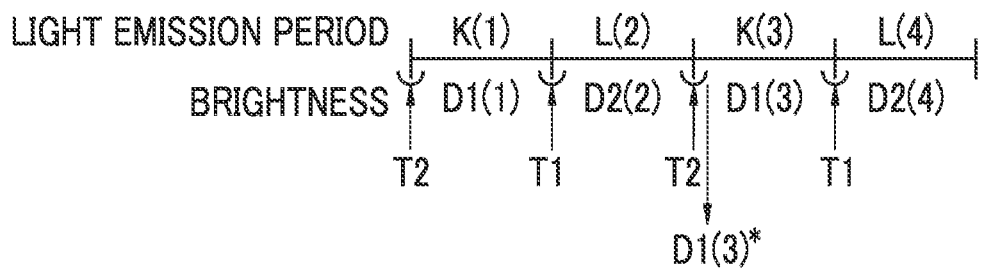
FIG. 21 is a diagram illustrating a light emission period and a brightness that show a first brightness D1(3)* used to adjust the amount of the second illumination light.

For example, in a case where the amount of the second illumination light set by the light amount-setting unit 56 is to be adjusted at a first switching timing T1 of a light emission period L(6) of the second illumination light as shown in FIG. 20, the amount of light is adjusted using a specific adjustment factor X that is based on a second brightness D2(4)* obtained at the first switching timing T1 of the light emission period L(4) before the light emission period L(6), a second brightness D2(2)* obtained at the first switching timing T1 of the light emission period L(2), and a target brightness V. Here, it is preferable that the specific adjustment factor X is obtained in a case where the target brightness V is divided by the value of the sum of the product of the second brightness D2(4)* and a weighting factor and the product of the second brightness D2(2)* and a weighting factor (specific adjustment factor X=V/(α1×D2(4)*+α2×D2(2)*). Here, α1 and α2 are weighting factors, and "α1+α2=1" is satisfied.

Further, in a case where the amount of the second illumination light set at the first switching timing T1 of the light emission period L(6) is defined as the amount H2(6) of light, the amount H2(6)* of the second illumination light having been subjected to the adjustment of the amount of light is obtained from the product of the specific adjustment factor X and the amount H2(6) of light (H2(6)*=X×H2(6)). The amount H2(6)* of the second illumination light having been subjected to the adjustment of the amount of light is sent to the light source controller 21, and the light source controller 21 controls the amount of the second illumination light on the basis of the amount H2(6)* of the second illumination light having been subjected to the adjustment of the amount of light.

The following generalized equation A) may be used to obtain the amount H2(N)* of light that is obtained in a case where the amount H2(N) of the second illumination light set at the first switching timing T1 of the light emission period L(N) is adjusted.

$$H2(N)^* = (\text{target brightness}) \times (\alpha 1/(\text{second brightness } D2(N-2) \text{ obtained at a first switching timing } T1 \text{ of a light emission period } L(N-2) + \alpha 2/(\text{second brightness } D2(N-4) \text{ obtained at a first switching timing } T1 \text{ of a light emission period } L(N-4) + \ldots + \alpha n/(\text{second brightness } D2(N-n) \text{ obtained at a first switching timing } T1 \text{ of a light emission period } L(N-n))$$ Equation A)

Here, "α1+α2+ ... αn=1" is satisfied. Further, n is an even number smaller than N.

Second Embodiment

In a second embodiment, the amount of second illumination light set at the first switching timing T1 of the light emission period L(N) is adjusted using information about a second switching timing T2 of a light emission period K(N−1) before the light emission period L(N) or the amount of first illumination light set at the second switching timing T2 of the light emission period K(N) is adjusted using information about a first switching timing T1 of a light emission period L(N−1) before the light emission period K(N).

For example, in a case where the amount of the second illumination light set by the light amount-setting unit 56 is to be adjusted at the first switching timing T1 of the light emission period L(4) of the second illumination light as shown in FIG. 20, the amount of light is adjusted using an adjustment factor Y(3) that is based on a first brightness D1(3)* obtained at the second switching timing T2 of the light emission period K(3) before the light emission period L(4) and a preset target brightness V. Here, it is preferable that the adjustment factor Y(3) is obtained in a case where the target brightness V is divided by the first brightness D1(3)* (adjustment factor Y(3)=V/D1(3)*).

That is, in a case where the amount of the second illumination light set at the first switching timing T1 of the light emission period L(4) is defined as the amount H2(4) of light, the amount H2(4)* of the second illumination light having been subjected to the adjustment of the amount of light is obtained from the product of the adjustment factor Y(3) and the amount H2(4) of light (H2(4)*=Y(3)×H2(4)). The amount H2(4)* of the second illumination light having been subjected to the adjustment of the amount of light is sent to the light source controller 21, and the light source controller 21 controls the amount of the second illumination light on the basis of the amount H2(4)* of the second illumination light having been subjected to the adjustment of the amount of light.

Further, the amount of the second illumination light set at the first switching timing T1 of the light emission period L(N) may be adjusted using information about second switching timings T2 of a plurality of light emission periods K(N-Q) and first switching timings T1 of a plurality of light emission periods L(N-P) before the light emission period L(N), or the amount of the first illumination light set at the second switching timing T2 of the light emission period K(N) may be adjusted using information about first switching timings T1 of a plurality of light emission periods L(N-Q) and second switching timings T2 of a plurality of light emission periods K(N-P) before the light emission period K(N). P is an even number smaller than N, and Q is an odd number smaller than N.

Figure 22:
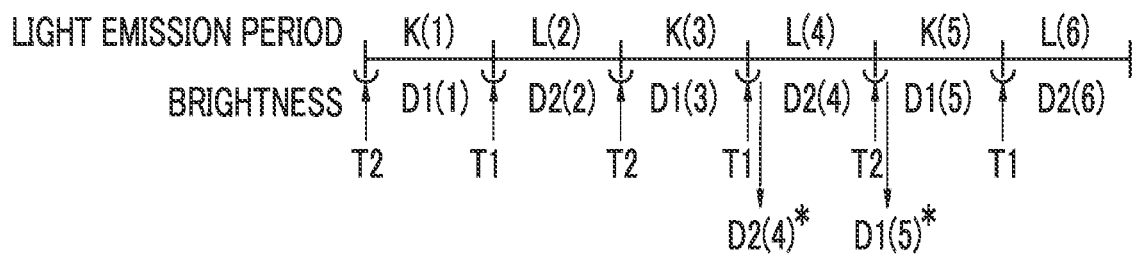
FIG. 22 is a diagram illustrating a light emission period and a brightness that show a second brightness D2(3)* and a first brightness D1(5)* used to adjust the amount of the second illumination light.

For example, in a case where the amount of the second illumination light set by the light amount-setting unit 56 is to be adjusted at the first switching timing T1 of a light emission period L(6) of the second illumination light as shown in FIG. 22, the amount of light is adjusted using a specific adjustment factor Y that is based on a first brightness D1(5)* obtained at a second switching timing T2 of a light emission period K(5) before the light emission period L(6), a second brightness D2(4)* obtained at the first switching timing T1 of the light emission period L(4), and a preset target brightness V.

Here, it is preferable that the specific adjustment factor Y is obtained in a case where a value obtained in a case where a value of the product of the first brightness D1(5)* and a weighting factor β is divided by the target brightness V is added to a value of the product of the second brightness D2(4)*, a weighting factor α, and the target brightness V (specific adjustment factor Y=β×D1(5)*/V+α×D2(4)*×V). Here, α and β are weighting factors, and "α+β=1" is satisfied.

Further, in a case where the amount of the second illumination light set at the first switching timing T1 of the light emission period L(6) is defined as the amount H2(6) of light, the amount H2(6)* of the second illumination light having been subjected to the adjustment of the amount of light is obtained from the product of the specific adjustment factor Y and the amount H2(6) of light (H2(6)*=Y×H2(6)). The amount H2(6)* of the second illumination light having been subjected to the adjustment of the amount of light is sent to the light source controller 21, and the light source controller 21 controls the amount of the second illumination light on the basis of the amount H2(6)* of the second illumination light having been subjected to the adjustment of the amount of light.

The following generalized equation B) may be used to obtain the amount H2(N)* of light that is obtained in a case where the amount H2(N) of the second illumination light set at the first switching timing T1 of the light emission period L(N) is adjusted.

$H2(N)^* = 1/(\text{target brightness}) \times (\beta 1/(\text{first brightness } D1(N-1) \text{ obtained at a second switching timing } T2 \text{ of a light emission period } K(N-1) + \beta 2/(\text{first brightness } D1(N-3) \text{ obtained at a second switching timing } T2 \text{ of a light emission period } K(N-3) + \ldots + \beta n/(\text{second brightness } D2(N-m) \text{ obtained at a first switching timing } T1 \text{ of a light emission period } (N-m) + (\text{target brightness}) \times (\alpha 1/(\text{second brightness } D2(N-2) \text{ obtained at a first switching timing } T1 \text{ of a light emission period } L(N-2) + \alpha 2/(\text{second brightness } D2(N-4) \text{ obtained at a first switching timing } T1 \text{ of a light emission period } L(N-4) + \ldots + \alpha n/(\text{second brightness } D2(N-n) \text{ obtained at a first switching timing } T1 \text{ of a light emission period } (N-n))$   Equation B)

Here, "α1+α2+ . . . αn=1" and "β1+β2+ . . . +βn=1" are satisfied. Further, n is an even number smaller than N, and m is an odd number smaller than N.

In the first and second embodiments, in the multi-observation mode, the amount of the second illumination light at the first switching timing T1 is always adjusted and the amount of the first illumination light at the second switching timing T2 is always adjusted. However, only in a case where the first brightness D1 or the second brightness is in a predetermined target brightness range, the amount of the second illumination light at the first switching timing T1 may be adjusted and the amount of the first illumination light at the second switching timing T2 may be adjusted.

For example, as shown in FIG. 16, in a case where the amount of the second illumination light set by the light amount-setting unit 56 is to be adjusted at the first switching timing T1 of the light emission period L(4) of the second illumination light, it is preferable that the amount of the second illumination light at the first switching timing T1 is not adjusted in a case where the second brightness D2(2)* is in a target brightness range, and the amount of the second illumination light at the first switching timing T1 is adjusted in a case where the second brightness D2(2)* is not in the target brightness range.

The hardware structures of the processing units included in the processor device 16 in the above-mentioned embodiments, such as the image acquisition unit 52, the DSP 54, the noise removing unit 58, the normal observation image processing unit 62, the special observation image processing unit 63, the display controller 64, the static image storage unit 65, and the static image-storage controller 66, are various processors to be described below. The various processors include: a central processing unit (CPU) that is a general-purpose processor functioning as various processing units by executing software (program); a programmable logic device (PLD) that is a processor of which circuit configuration can be changed after manufacture, such as a field programmable gate array (FPGA); a graphical processing unit (GPU); a dedicated electrical circuit that is a processor having circuit configuration designed exclusively to perform various kinds of processing; and the like.

One processing unit may be formed of one of these various processors, or may be formed of a combination of two or more same kind or different kinds of processors (for example, a plurality of FPGAs, a combination of a CPU and an FPGA, or a combination of a CPU and a GPU). Further, a plurality of processing units may be formed of one processor. As an example where a plurality of processing units are formed of one processor, first, there is an aspect where one processor is formed of a combination of one or more CPUs and software as typified by a computer, such as a client or a server, and functions as a plurality of processing units. Second, there is an aspect where a processor fulfilling the functions of the entire system, which includes a plurality of processing units, by one integrated circuit (IC) chip as typified by System On Chip (SoC) or the like is used. In this way, various processing units are formed of one or more of the above-mentioned various processors as hardware structures.

In addition, the hardware structures of these various processors are more specifically electrical circuitry where circuit elements, such as semiconductor elements, are combined.

The invention can be applied to a processor device, which is combined with a capsule endoscope system, or various medical image processing devices in addition to the processor device that is combined with the endoscope system described in the first or second embodiment.

EXPLANATION OF REFERENCES

10: endoscope system
12: endoscope
12a: insertion part
12b: operation part
12c: bendable part
12d: distal end part 12e: angle knob
13a: mode changeover SW
13b: static image-acquisition instruction unit
14: light source device
16: processor device
18: monitor
19: user interface
20: light source unit
20a: violet light emitting diode (V-LED)
20b: blue light emitting diode (B-LED)
20c: green light emitting diode (G-LED)
20d: red light emitting diode (R-LED)
21: light source controller
23: optical path-combination unit
24: light emission period-setting unit
26a: slide bar
26b: slide bar
27a: slider
27b: slider
30a: illumination optical system
30b: image pickup optical system
41: light guide
45: illumination lens
46: objective lens
48: image pickup sensor
48b: B-filter
48g: G-filter
48r: R-filter
50: CDS/AGC circuit
52: image acquisition unit
54: digital signal processor (DSP)
55: brightness calculation unit
56: light amount-setting unit
57: set light amount-adjustment unit
58: noise removing unit
60: signal switching unit
62: normal observation image processing unit
63: special observation image processing unit
64: display controller
65: static image storage unit
66: static image-storage controller
67: first special observation image processing unit
68: second special observation image processing unit
69: detection unit
SP1: first special observation image (first image)
SP2: second special observation image (second image)
VP: violet light image
GRP: green-red light image
VS1: superficial blood vessel
VS2: deep blood vessel
BM: background mucous membrane

What is claimed is:

1. An endoscope system comprising:
a light source unit that emits first illumination light and second illumination light having an emission spectrum different from an emission spectrum of the first illumination light;
a first processor; and
a second processor,
wherein, in a case where the first processor performs control to automatically switch and emit the first illumination light and the second illumination light, each of a light emission period K(N) in which the first illumination light is emitted and a light emission period L(N) in which the second illumination light is emitted is a light emission period of at least one or more frames,
the second processor acquires a first image signal group that includes first image signals obtained through image pickup of a subject illuminated with the first illumination light in the light emission period K(N) of the first illumination light and a second image signal group that includes second image signals obtained through image pickup of the subject illuminated with the second illumination light in the light emission period L(N) of the second illumination light, calculates a first brightness D1 of the subject from the first image signals and calculates a second brightness D2 of the subject from the second image signals, sets an amount of the first illumination light or the second illumination light on a basis of the first brightness or the second brightness, and performs at least one of adjustment of the amount of the second illumination light that is set at a first switching timing at which illumination light is switched to the second illumination light from the first illumination light or adjustment of the amount of the first illumination light that is set at a second switching timing at which illumination light is switched to the first illumination light from the second illumination light, and
the second processor performs at least one of adjustment of an amount of the second illumination light, which is set at a first switching timing T1 of the light emission period L(N), using information about a first switching timing T1 of a light emission period L(N−2) before the light emission period L(N) or adjustment of an amount of the first illumination light, which is set at a second switching timing T2 of the light emission period K(N), using information about a second switching timing T2 of a light emission period K(N−2) before the light emission period K(N).

2. The endoscope system according to claim 1, wherein, in a case where N is set to 4 and an amount of the second illumination light set at a first switching timing T1 of a light emission period L(4) is to be adjusted, the amount of the second illumination light is multiplied by an adjustment factor X(2), which is obtained in a case where a preset target brightness is divided by a second brightness D2(2)* obtained at the first switching timing T1, as information about a first switching timing T1 of a light emission period L(2).

3. The endoscope system according to claim 1, wherein the second processor performs at least one of adjustment of an amount of the second illumination light, which is set at a first switching timing T1 of the light emission period L(N), using information about first switching timings T1 of a plurality of light emission periods L(N-P) before the light emission period L(N) or adjustment of an amount of the first illumination light, which is set at a second switching timing T2 of the light emission period K(N), using information about second switching timings T2 of light emission periods K(N-P) before the light emission period K(N).

4. The endoscope system according to claim 3, wherein a second brightness D2 obtained at the first switching timing T1 includes a plurality of second brightnesses D2(N-P) indicating second brightnesses obtained at the first switching timings T1 of the plurality of light emission periods L(N-P), respectively, and
in a case where the second processor adjusts the amount of the second illumination light set at the first switching timing T1 of the light emission period L(N), the amount of the second illumination light is multiplied by a specific adjustment factor X, which is obtained in a case where a preset target brightness is divided by a value of a sum of products of the plurality of second brightnesses D2(N-P) and weighting factors, as the information about the first switching timings T1 of the plurality of light emission periods L(N-P).

5. The endoscope system according to claim 1,
wherein the second processor performs at least one of adjustment of an amount of the second illumination light, which is set at a first switching timing T1 of the light emission period L(N), using information about a second switching timing T2 of a light emission period K(N−1) before the light emission period L(N) or adjustment of an amount of the first illumination light, which is set at a second switching timing T2 of the light emission period K(N), using information about a first switching timing T1 of a light emission period L(N−1) before the light emission period K(N).

6. The endoscope system according to claim 5,
wherein, in a case where N is set to 4 and an amount of the second illumination light set at a first switching timing T1 of a light emission period L(4) is to be adjusted, the amount of the second illumination light is multiplied by an adjustment factor Y(3), which is obtained in a case where a first brightness D1(3)* obtained at a second switching timing T2 of a light emission period K(3) is divided by a preset target brightness, as the information about the second switching timing T2 of the light emission period K(3).

7. The endoscope system according to claim 1,
wherein the second processor performs at least one of adjustment of an amount of the second illumination light, which is set at a first switching timing T1 of the light emission period L(N), using information about second switching timings T2 of a plurality of light emission periods K(N-Q) and first switching timings T1 of a plurality of light emission periods L(N-P) before the light emission period L(N) or adjustment of an amount of the first illumination light, which is set at a second switching timing T2 of the light emission period K(N), using information about first switching timings T1 of a plurality of light emission periods L(N-Q) and second switching timings T2 of a plurality of light emission periods K(N-P) before the light emission period K(N).

8. The endoscope system according to claim 7,
wherein, in a case where N is set to 6 and the second processor adjusts an amount of the second illumination light set at a first switching timing T1 of a light emission period L(6), an amount of the second illumination light is multiplied by a specific adjustment factor Y that is based on a first brightness D1(5)* obtained at a second switching timing T2 of a light emission period K(5), a second brightness D2(4)* obtained at a first switching timing T1 of a light emission period L(4), and a preset target brightness V.

9. The endoscope system according to claim 1,
wherein the first brightness or the second brightness is obtained on a basis of an average of pixel values of portions other than blood vessels or a lesion among the first image signals or the second image signals.

10. The endoscope system according to claim 1,
wherein the first brightness or the second brightness is obtained on a basis of an average of pixel values of pixels other than abnormal pixels, which include at least one of a dark portion or a halation, among the first image signals or the second image signals or on a basis of an average of pixel values of normal image signals other than the first image signals or the second image signals, which include the abnormal pixels, of the first image signal group or the second image signal group.

11. The endoscope system according to claim 1,
wherein the second processor adjusts the amount of the second illumination light or adjusts the amount of the first illumination light only in a case where the first brightness or the second brightness is in a predetermined target brightness range.

* * * * *